US010519206B2

(12) United States Patent
Noelke et al.

(10) Patent No.: US 10,519,206 B2
(45) Date of Patent: Dec. 31, 2019

(54) GENETICALLY MODIFIED HIGHER PLANTS WITH INCREASED PHOTOSYNTHESIS AND/OR BIOMASS PRODUCTION, METHODS AND USES THEREOF

(71) Applicant: Fraunhofer-Gesellschaft zur Foerderung der angewandten Forschung e.V., Munich (DE)

(72) Inventors: Greta Noelke, Aachen (DE); Stefan Schillberg, Aachen (DE); Fritz Kreutzaler, Aachen (DE); Mirna Barsoum, Eschweiler (DE); Rainer Fischer, Aachen (DE)

(73) Assignee: Fraunhofer-Gesellschaft Zur Förderung Der Angewandten Forschung E.V., Munich (DE)

( * ) Notice: Subject to any disclaimer, the term of this patent is extended or adjusted under 35 U.S.C. 154(b) by 246 days.

(21) Appl. No.: 15/532,082

(22) PCT Filed: Nov. 26, 2015

(86) PCT No.: PCT/EP2015/077803
§ 371 (c)(1),
(2) Date: May 31, 2017

(87) PCT Pub. No.: WO2016/087314
PCT Pub. Date: Jun. 9, 2016

(65) Prior Publication Data
US 2017/0283473 A1 Oct. 5, 2017

(51) Int. Cl.
| C07K 14/415 | (2006.01) |
| C12N 15/82 | (2006.01) |
| C12N 1/12 | (2006.01) |
| C12N 15/74 | (2006.01) |
| C12N 15/79 | (2006.01) |
| C12N 15/09 | (2006.01) |

(52) U.S. Cl.
CPC .............. *C07K 14/415* (2013.01); *C12N 1/12* (2013.01); *C12N 15/74* (2013.01); *C12N 15/79* (2013.01); *C12N 15/8261* (2013.01); *C12N 15/8265* (2013.01); *C12N 15/09* (2013.01); *C12N 15/82* (2013.01)

(58) Field of Classification Search
CPC .................................................... C07K 14/415
See application file for complete search history.

(56) References Cited

U.S. PATENT DOCUMENTS 10,233,458 B2 * 3/2019 Sayre ..................... C12P 1/00
2013/0007916 A1 1/2013 Spalding

FOREIGN PATENT DOCUMENTS

WO 2012125737 A2 9/2012

OTHER PUBLICATIONS

Price, G.D. et al. Plant Physiology, Jan. 2011; vol. 155, pp. 20-26.*
PCT/EP2015/077803 International Search Report dated Jun. 20, 2016.
Miura et al. "Expression Profiling-Based Identification of CO2-Responsive Genes Regulated by CCM1 Controlling a Carbon-Concentrating Mechanism in Chlamydomonas reinhardtii." Plant Physiology, Jul. 2004, 135(3):1595-1607.
Wang and Spalding. "Acclimation to Very Low CO2: Contribution of Limiting CO2 Inducible Proteins, LCIB and LCIA, to Inorganic Carbon Uptake in Chlamydomonas reinhardtii" Plant Physiology, Dec. 2014, 166(4): 2040-2050.

* cited by examiner

*Primary Examiner* — Russell Kallis
(74) *Attorney, Agent, or Firm* — Wagenknecht IP Law Group PC

(57) ABSTRACT

The technology provided herein generally relates relates to genetically modified higher plants, for example C3 and C4 plants, and subsequent generations thereof, comprising stable and/or transient expression of at least one gene-product (e.g. mRNA or protein) of the "*Chlamydomonas reinhardtii* $CO_2$ concentrating mechanism" (CCM), wherein the expression takes place in the intermembrane space and/or one or more subcellular compartments of the chloroplasts of the higher plant, and wherein this expression increases one or more of the characteristics selected from the group of photosynthetic rate, photosynthetic carbon fixation, chlorophyll level and/or biomass of the genetically modified higher plant (T0) and/or of the T1 and/or T2 generation or any subsequent plant generation of said genetically modified higher plant.

18 Claims, 19 Drawing Sheets
Specification includes a Sequence Listing.

FIGURE 8
A)
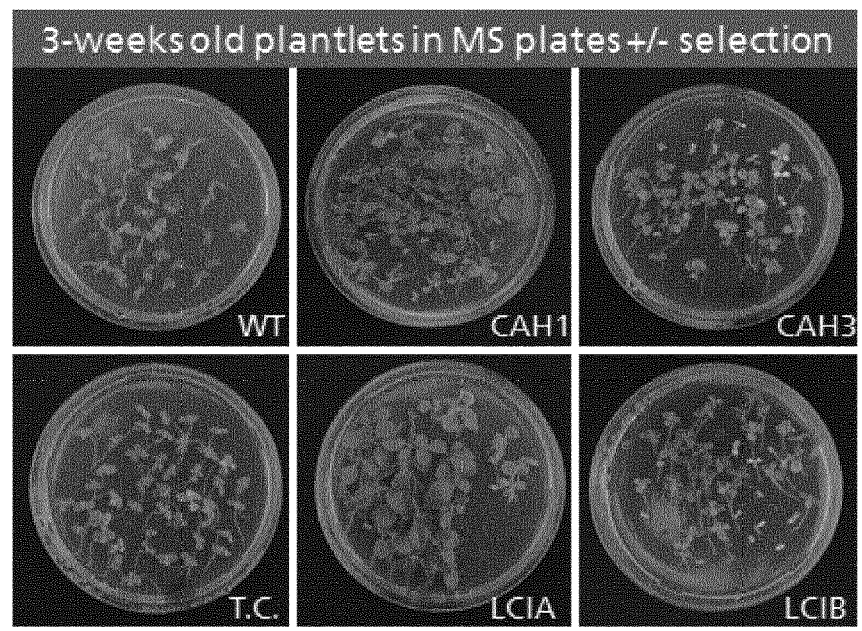
B)
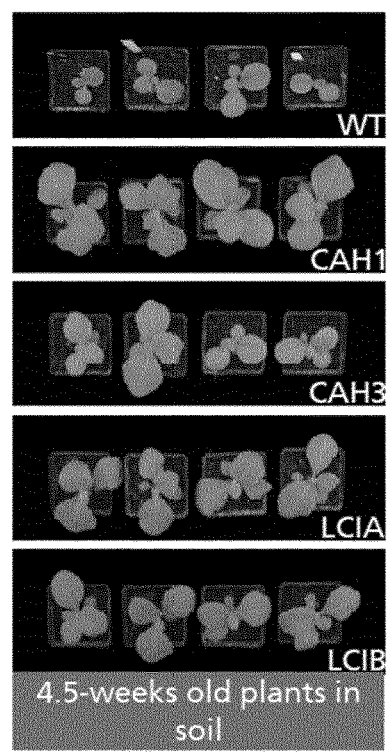

FIGURE 9
A)
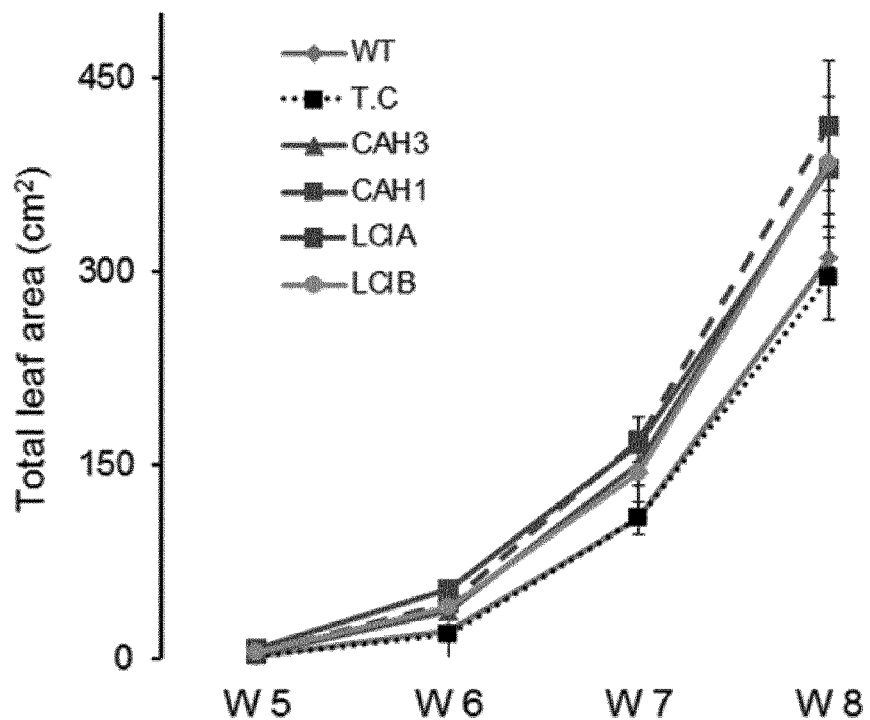
B)
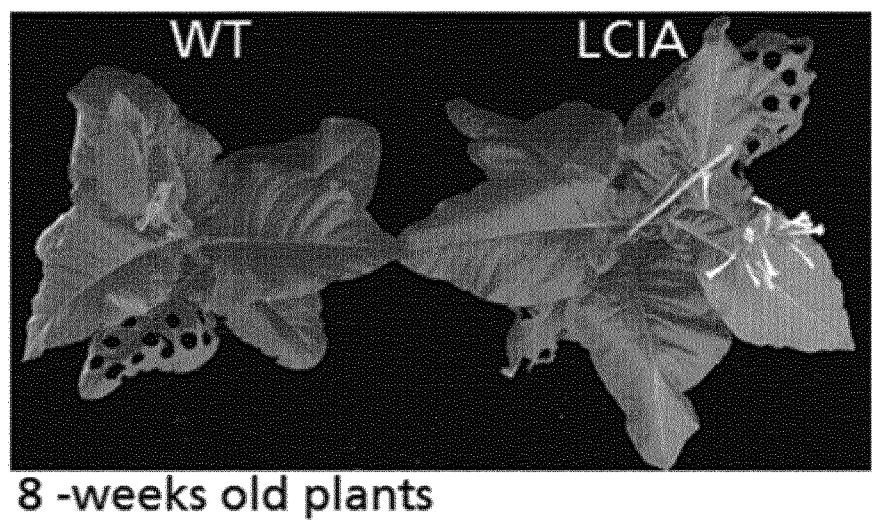

FIGURE 13

Table 4

| Photosynthesis parameter | Tobacco lines | | | | |
|---|---|---|---|---|---|
| | WT | CAH1 | CAH3 | LCIA | LCIB |
| $A_{max}$ (μmol m$^{-2}$ s$^{-1}$) (at $C_a$ = 400 p.p.m) | 20.6 ± 0.5 | 23.1 ± 1.4*<br>12.4% ↑ | 23.4 ± 1.1*<br>14% ↑ | 22.4 ± 1*<br>9% ↑ | 22.7 ± 1.1*<br>10% ↑ |
| $A_{max}$ (μmol m$^{-2}$ s$^{-1}$) (at $C_a$ = 1000 p.p.m) | 30.6 ± 1.7 | 30.5 ± 0.4 | 30.2 ± 1.1 | 30 ± 1.1 | 32 ± 1 |
| Γ (p.p.m $CO_2$) | 66 ± 2 | 64.6 ±1.6<br>1.9% ↓ | 64 ± 1.2*<br>3% ↓ | 64.6 ± 1.2*<br>2% ↓ | 64 ± 1.1<br>2.7% ↓ |
| ETR/A (at C = 400-80) | | n.s | n.s | n.s | n.s |
| Conductance (at Ca = 400) | 0.29 ± 0.05 | 0.33 ± 0.04<br>11% ↑ | 0.38 ± 0.06*<br>27% ↑ | 0.39 ± 0.06*<br>33% ↑ | 0.31 ± 0.09 |
| Transpiration (at Ca = 400) | 3.93 ± 0.58 | 3.98 ± 0.5 | 4.55 ± 0.5*<br>16% ↑ | 4.4 ± 0.6<br>14% ↑ | 4 ± 0.6 |
| Chlorophyll | 36.6 ± 0.86 | 41.26 ± 0.81<br>13% ↑ | 40.9 ± 1.1<br>12 % ↑ | 39.4 ± 0.9<br>8 % ↑ | 40.4 ± 1.4<br>10% ↑ |

- All transgenic lines have higher levels of $CO_2$ in the vicinity of Rubisco
- Increased stomata conduction – improved $CO_2$ uptake.

FIGURE 14

CAH1

ATGGAGTCAAGCGTTAAGCCAAACCCATTCCTCTCATTTTCTTCTTTTATTCATCACCAATGTACTAGATTCAGTA
GCGATTTGAGTGCTAGAATCGAAGATACAAAGAGGTTTGCTGAGACTCTTGCAACAAGAAGGTTTTCTTTGCC
TACTCCACCTCCATTCGCTTCCGTTTCCATGGGGTGTATCTATAAGTTCGGTACTAGCCCAGATTCCAAAGCAAC
AGTGTCTGGAGATCATTGGGATCACGGACTTAATGGTGAAAACTGGGAGGGAAAAGATGGAGCTGGTAATGC
ATGGGTGTGCAAGACAGGTAGAAAGCAATCACCAATTAATGTTCCACAATATCAGGTGTTGGATGGAAAGGG
TTCAAAAATTGCTAATGGTCTTCAAACTCAGTGGAGTTACCCTGATTTGATGTCTAACGGAACATCAGTTCAAG
TTATTAATAACGGACATACTATACAAGTTCAGTGGACATACAACTACGCTGGTCATGCAACTATTGCTATCCCA
GCAATGCACAATCAAACAAACAGGATTGTTGATGTGCTTGAAATGAGACCTAATGATGCTGCAGATAGGGTTA
CTGCTGTGCCAACACAGTTTCACTTCCATTCAACTAGTGAACATCTTTTGGCAGGAAAGATCTATCCTTTAGAGC
TCCATATAGTTCACCAAGTGACTGAAAAGCTTGAGGCTTGTAAAGGAGGTTGCTTTAGTGTTACAGGAATCCTT
TTCCAGTTGGATAATGGTCCAGATAACGAACTCCTTGAACCTATATTCGCTAATATGCCAAGTAGAGAAGGTAC
TTTCAGCAACTTACCTGCAGGAACTACAATTAAGCTCGGAGAGCTTTTGCCATCTGATAGGGATTATGTTACTT
ACGAAGGATCTCTTACTACACCTCCATGTTCTGAGGGTTTACTCTGGCATGTGATGACACAACCTCAGAGAATT
TCTTTTGGACAGTGGAATAGATACAGATTAGCTGTTGGTCTCAAAGAATGCAACTCAACTGAGACAGCTGCAG
ATGCTGGACATCACCATCACCATAGAAGGCTTTTGCACAATCATGCACACTTAGAAGAGGTTCCTGCTGCAACT
AGCGAACCAAAGCATTATTTTAGAAGAGTTATGCTTGCTGAGTCTGCAAATCCAGATGCATACACATGCAAAG
CTGTTGCATTCGGTCAAAACTTTAGGAACCCTCAGTATGCTAACGGAAGAACTATCAAGCTCGCTAGGTATCAT

FIGURE 15

CAH3

ATGAGGTCCGCAGTGCTCCAAAGGGGTCAGGCAAGAAGAGTTTCTTGTAGAGTGAGGGCTGATGGATCTGGT
GTTGATTCACTTCCAAGCACTTCCGCTTCTTCAAGTGCAAGACCTTTGATCGATAGAAGGCAACTTTTGACTGG
AGCTGCAGCTTCAGTTATAACATTTGTGGGATGTCCATGCCCTCTTTGTAAGCCAGGTGAAGCTAAAGCAGCTG
CATGGAATTATGGAGAGGTTGCAGGTCCACCTACTTGGAAGGGAGTGTGCGCTACAGGAAAGAGACAGTCCC
CAATTAATATCCCTCTTAACACATCTGCACCTAAGGTTGATGCTGAAATGGGAGAGTTTGATTTCGCTTACGGTT
CATTCGAAAAATGCGATGTTTTGAATACTGGACATGGTACAATGCAAGTTGTGAATTTTCCAGCTGGAAACTTA
GCATTCATTGGTAACATGGAACTTGAATTACTCCAGTTTCATTTCCACGCACCTAGCGAACATGCTATGGATGG
AAGAAGATATGCTATGGAGGCACATCTTGTTCACAAGAATAAGAGTACTGGACACTTAGCAGTGCTCGGTATT
ATGCTCCAGGAGGTGCTGATCAAAACCCTGCTCTTTCTACAGCATTGGAAGTTGCTCCAGAGGTGCCTTTGGC
AAAGAAACCATCACCTAAGGGTATCAATCCAGTTATGCTTTTGCCTAAGAAAAGTAAAGCTGGAACTAGACCA
TTTGTGCACTACCCTGGTAGTTTGACTACACCACCTTGTAGCGAGGGAGTTGATTGGTTTGTGTTCATGCAACC
AATTAAGGTTCCTGATTCTCAGATCCTCGATTTCATGAGGTTCGTGGGAGATAACAAAACATATGCTACTAACA
CAAGACCATTACAACTCCTCAACTCAAGACTCGTGGAATATGAACTC

FIGURE 16

LCIA

ATGCAGACTACAATGACAAGACCATGTTTAGCACAGCCAGTTCTTAGATCCAGGGTGTTGAGATCTCCTATGA
GGGTTGTGGCTGCATCCGCTCCAACTGCAGTTACTACAGTTGTGACATCTAATGGTAACGGTAATGGTCATTTC
CAAGCTGCAACTACACCTGTTCCACCTACACCAGCTCCTGTTGCAGTGTCAGCTCCAGTGAGGGCTGTTAGTGT
GTTGACTCCACCTCAGGTTTATGAAAACGCAATTAATGTGGGAGCATACAAAGCTGGTCTTACTCCTTTGGCTA
CATTTGTTCAAGGAATACAGGCTGGTGCATATATCGCATTCGGAGCTTTTCTTGCAATTTCAGTTGGTGGTAAC
ATACCTGGAGTGGCTGCAGCTAATCCAGGTCTTGCTAAGCTTTTGTTCGCATTAGTTTTTCCAGTGGGACTCAG
TATGGTTACTAACTGTGGAGCTGAACTTTTCACTGGTAATACAATGATGCTTACATGCGCTTTGATTGAGAAGA
AAGCAACTTGGGGTCAATTACTCAAAAACTGGTCTGTTTCATACTTCGGAAATTTTGTTGGTTCAATAGCTATG
GTGGCAGCTGTTGTGGCAACTGGATGTTTAACTACAAACACACTCCCTGTGCAGATGGCTACTTTAAAGGCAA
ATCTCGGTTTTACAGAAGTTCTTAGTAGGTCCATACTTTGTAATTGGTTGGTTTGTTGCGCTGTGTGGTCTGCAT
CAGCAGCTACATCTTTGCCTGGAAGAATCCTTGCTTTGTGGCCATGCATCACTGCTTTCGTTGCAATTGGTCTTG
AACATTCAGTTGCTAACATGTTTGTGATTCCTTTAGGAATGATGCTCGGTGCAGAGGTTACTTGGAGTCAATTT
TTCTTTAATAACCTTATCCCAGTTACTTTGGGAAATACAATCGCTGGTGTGCTTATGATGGCTATAGCATACAGT
ATCTCCTTCGGATCATTGGGAAAGTCTGCAAAACCAGCTACAGCA

FIGURE 17

LCIB

ATGTTCGCACTCAGTTCAAGACAGACAGCAAGGTCCGCATGTAGAGCATCTTGTCCATGCGCTTCATGCAGGG
GTGTGGCTAGTGCACCAGTTAGAGCAACATATGCTGCAAGGCCTGTTAAGAAATCTGCTGCATCAGTTGTGGT
TAAGGCTCAAGCTGCATCTACTGCTGTGGCACCAGTTGAGAATGGTGCTGCACCTGCTGTTGCACATAAGAGA
ACATTTGCTCAGAGGCATAGTGAATTGATTAAACACTTTCCTTCCACCATGGGCGTTGATGATTTCATGGGTAG
AGTGGAGGTTGCTCTTGCAGGATTTGGTTTCACTGGAGATAATACAATTGCAATGACTAACCTCTGTAGGGAT
GAAGTGACACAAGTTCTTAAGGATAAAATCGAGGCTATTTTTGGATCTTCATTCAATACTAACGGTCTTGGTGG
TGTGTTGACATGTGGAGTTACTGGTATGAAAGCTGGATTGTCTCATTCACCAGTGTGCAATGGTGGAAGAGAA
AGATATGTTTTCTTTGCATTTCCTCACATTGCTATTAATTCTGAAGGAGAGATGGGTGCACTTTCAAGACCTGGT
AGGCCTAAGCAAAGTTGTGCTTGCGGAGCACTTTTGGCTATTCTTAATGCTTTCAAAGTGGATGGTGTTGAAAA
GTCATGTAAAGTGCCAGGAGTTCACGATCCACTTGATCCTGAGTTAACAATACTCCAACAGAGATTGGCTAGA
AGGGTGAGGTATGAAAAGTTAGATGTTTCCAAACTTGATTTGCCAGGTTTGACTTCTGTTGCTGAAAGAACTAT
AACAGATGATCTTGAATATTTGATAGAGAAGGCAGTTGATCCAGCTGTTGCAGATTACGCTGTGATAACAGGA
GTTCAAATCCATAATTGGGGTAAAGAACTTAGTGCATCCGGAGATGCTTCTATTGAGTTTGTTGCTCCAGCAAA
GTGCTATACAGTGGTTAACGGTCTTAAAACTTACATAGATTTGCCACAGGTTCCTGCTTTATCACCTAGACAAAT
CCAGACAATGGCTCAAGCAAGTCTTAATGGTTTCGAACCAAAGCACATCCAGCCTGGAATGAGGGGTAGTGTG
ATTTCCGAAGTTCCTTTAGAGTATCTCGTTACTAAATTAGGAGGTTCCCAACTCATGGAGGATGGAAACTCTTA
CGCACCAGTTTTTGCTAGTTCCGATTCATTCGAATGGCCTACATGGCAGAGTAGAATTAGGCTTGATAATAACC
CAAACAGATTACTCTCTGTGGAGAGGGATGCTAACGCACCTACTATGGAATCACCAGAGCCTGTTCACCCTAGT
TTTGAGGCACCTAAGAATAAG

SEQUENCE LISTING

```
<160> NUMBER OF SEQ ID NOS: 5

<210> SEQ ID NO 1
<211> LENGTH: 1254
<212> TYPE: DNA
<213> ORGANISM: Chlamydomonas reinhardtii

<400> SEQUENCE: 1
atggagtcaa gcgttaagcc aaacccattc ctctcatttt cttcttttat tcatcaccaa    60
tgtactagat tcagtagcga tttgagtgct agaatcgaag atacaaagag gtttgctgag   120
actcttgcaa caagaaggtt ttctttgcct actccacctc cattcgcttc cgtttccatg   180
gggtgtatct ataagttcgg tactagccca gattccaaag caacagtgtc tggagatcat   240
tgggatcacg gacttaatgg tgaaaactgg gagggaaaag atggagctgg taatgcatgg   300
gtgtgcaaga caggtagaaa gcaatcacca attaatgttc cacaatatca ggtgttggat   360
ggaaagggtt caaaaattgc taatggtctt caaactcagt ggagttaccc tgatttgatg   420
tctaacggaa catcagttca agttattaat aacggacata ctatacaagt tcagtggaca   480
tacaactacg ctggtcatgc aactattgct atcccagcaa tgcacaatca aacaaacagg   540
attgttgatg tgcttgaaat gagacctaat gatgctgcag ataggttac tgctgtgcca   600 acacagtttc acttccattc aactagtgaa catcttttgg caggaaagat ctatccttta   660
gagctccata tagttcacca agtgactgaa aagcttgagg cttgtaaagg aggttgcttt   720
```

| | |
|---|---|
| agtgttacag gaatccttttt ccagttggat aatggtccag ataacgaact ccttgaaccct | 780 |
| atattcgcta atatgccaag tagagaaggt actttcagca acttacctgc aggaactaca | 840 |
| attaagctcg gagagctttt gccatctgat agggattatg ttacttacga aggatctctt | 900 |
| actacacctc catgttctga gggtttactc tggcatgtga tgacacaacc tcagagaatt | 960 |
| tcttttggac agtggaatag atacagatta gctgttggtc tcaaagaatg caactcaact | 1020 |
| gagacagctg cagatgctgg acatcaccat caccatagaa ggcttttgca caatcatgca | 1080 |
| cacttagaag aggttcctgc tgcaactagc gaaccaaagc attattttag aagagttatg | 1140 |
| cttgctgagt ctgcaaatcc agatgcatac acatgcaaag ctgttgcatt cggtcaaaac | 1200 |
| tttaggaacc ctcagtatgc taacggaaga actatcaagc tcgctaggta tcat | 1254 |

<210> SEQ ID NO 2
<211> LENGTH: 930
<212> TYPE: DNA
<213> ORGANISM: Chlamydomonas reinhardtii

<400> SEQUENCE: 2

| | |
|---|---|
| atgaggtccg cagtgctcca aaggggtcag gcaagaagag tttcttgtag agtgagggct | 60 |
| gatggatctg tgttgattc acttccaagc acttccgctt cttcaagtgc aagaccttg | 120 |
| atcgatagaa ggcaacttt gactggagct gcagcttcag ttataacatt tgtgggatgt | 180 |
| ccatgccctc tttgtaagcc aggtgaagct aaagcagctg catggaatta tggagaggtt | 240 |
| gcaggtccac ctacttggaa gggagtgtgc gctacaggaa agagacagtc cccaattaat | 300 |
| atccctctta acacatctgc acctaaggtt gatgctgaaa tgggagagtt tgatttcgct | 360 |
| tacggttcat tcgaaaaatg cgatgttttg aatactggac atggtacaat gcaagttgtg | 420 |
| aattttccag ctggaaactt agcattcatt ggtaacatgg aacttgaatt actccagttt | 480 |
| catttccacg cacctagcga acatgctatg gatggaagaa gatatgctat ggaggcacat | 540 |
| cttgttcaca agaataagag tactggacac ttagcagtgc tcggtattat gctcccagga | 600 |
| ggtgctgatc aaaaccctgc tctttctaca gcattggaag ttgctccaga ggtgcctttg | 660 |
| gcaaagaaac catcacctaa gggtatcaat ccagttatgc ttttgcctaa gaaaagtaaa | 720 |
| gctggaacta gaccatttgt gcactaccct ggtagtttga ctacaccacc ttgtagcgag | 780 |
| ggagttgatt ggtttgtgtt catgcaacca attaaggttc ctgattctca gatcctcgat | 840 |
| tcatgaggt tcgtgggaga taacaaaaca tatgctacta acacaagacc attacaactc | 900 |
| ctcaactcaa gactcgtgga atatgaactc | 930 |

<210> SEQ ID NO 3
<211> LENGTH: 1008
<212> TYPE: DNA
<213> ORGANISM: Chlamydomonas reinhardtii

<400> SEQUENCE: 3

| | |
|---|---|
| atgcagacta caatgacaag accatgttta gcacagccag ttcttagatc cagggtgttg | 60 |
| agatctccta tgagggttgt ggctgcatcc gctccaactg cagttactac agttgtgaca | 120 |
| tctaatggta acgtaatgg tcatttccaa gctgcaacta cacctgttcc acctacacca | 180 |
| gctcctgttg cagtgtcagc tccagtgagg gctgttagtg tgttgactcc acctcaggtt | 240 |
| tatgaaaacg caattaatgt gggagcatac aaagctggtc ttactccttt ggctacattt | 300 |
| gttcaaggaa tacaggctgg tgcatatatc gcattcggag cttttcttgc aatttcagtt | 360 |
| ggtggtaaca tacctggagt ggctgcagct aatccaggtc ttgctaagct tttgttcgca | 420 |

| | | |
|---|---|---|
| ttagtttttc cagtgggact cagtatggtt actaactgtg gagctgaact tttcactggt | 480 |
| aatacaatga tgcttacatg cgctttgatt gagaagaaag caacttgggg tcaattactc | 540 |
| aaaaactggt ctgtttcata cttcggaaat tttgttggtt caatagctat ggtggcagct | 600 |
| gttgtggcaa ctggatgttt aactacaaac acactccctg tgcagatggc tactttaaag | 660 |
| gcaaatctcg gttttacaga agttcttagt aggtccatac tttgtaattg gttggtttgt | 720 |
| tgcgctgtgt ggtctgcatc agcagctaca tctttgcctg aagaatcct tgctttgtgg | 780 |
| ccatgcatca ctgctttcgt tgcaattggt cttgaacatt cagttgctaa catgtttgtg | 840 |
| attcctttag gaatgatgct cggtgcagag gttacttgga gtcaattttt ctttaataac | 900 |
| cttatcccag ttactttggg aaatacaatc gctggtgtgc ttatgatggc tatagcatac | 960 |
| agtatctcct tcggatcatt gggaaagtct gcaaaaccag ctacagca | 1008 |

<210> SEQ ID NO 4
<211> LENGTH: 1347
<212> TYPE: DNA
<213> ORGANISM: Chlamydomonas reinhardtii

<400> SEQUENCE: 4

| | | |
|---|---|---|
| atgttcgcac tcagttcaag acagacagca aggtccgcat gtagagcatc ttgtccatgc | 60 |
| gcttcatgca ggggtgtggc tagtgcacca gttagagcaa catatgctgc aaggcctgtt | 120 |
| aagaaatctg ctgcatcagt tgtggttaag gctcaagctg catctactgc tgtggcacca | 180 |
| gttgagaatg tgctgcacc tgctgttgca cataagagaa catttgctca gaggcatagt | 240 |
| gaattgatta aacactttcc ttccaccatg ggcgttgatg atttcatggg tagagtggag | 300 |
| gttgctcttg caggatttgg tttcactgga gataatacaa ttgcaatgac taacctctgt | 360 |
| agggatgaag tgacacaagt tcttaaggat aaaatcgagg ctattttgg atcttcattc | 420 |
| aatactaacg tcttggtgg tgtgttgaca tgtggagtta ctggtatgaa agctggattg | 480 |
| tctcattcac cagtgtgcaa tggtggaaga gaaagatatg ttttctttgc atttcctcac | 540 |
| attgctatta attctgaagg agagatgggt gcactttcaa gacctggtag gcctaagcaa | 600 |
| agttgtgctt gcggagcact tttggctatt cttaatgctt tcaaagtgga tggtgttgaa | 660 |
| aagtcatgta agtgccagg agttcacgat ccacttgatc ctgagttaac aatactccaa | 720 |
| cagagattgg ctagaagggt gaggtatgaa aagttagatg tttccaaact tgatttgcca | 780 |
| ggtttgactt ctgttgctga agaactata acagatgatc ttgaatattt gatagagaag | 840 |
| gcagttgatc cagctgttgc agattacgct gtgataacag gagttcaaat ccataattgg | 900 |
| ggtaaagaac ttagtgcatc cggagatgct tctattgagt tgttgctcc agcaaagtgc | 960 |
| tatacagtgg ttaacggtct taaaacttac atagatttgc cacaggttcc tgctttatca | 1020 |
| cctagacaaa tccagacaat ggctcaagca agtcttaatg gtttcgaacc aaagcacatc | 1080 |
| cagcctggaa tgaggggtag tgtgatttcc gaagttcctt tagagtatct cgttactaaa | 1140 |
| ttaggaggtt cccaactcat ggaggatgga aactcttacg caccagtttt tgctagttcc | 1200 |
| gattcattcg aatggcctac atggcagagt agaattaggc ttgataataa cccaaacaga | 1260 |
| ttactctctg tggagaggga tgctaacgca cctactatgg aatcaccaga gcctgttcac | 1320 |
| cctagttttg aggcacctaa gaataag | 1347 |

<210> SEQ ID NO 5
<211> LENGTH: 8882
<212> TYPE: DNA

<213> ORGANISM: Artificial Sequence
<220> FEATURE:
<223> OTHER INFORMATION: Vectorconstruct pTRA-35S-AtTic22-TP:CAH1

<400> SEQUENCE: 5

```
aattccgccc ctagaaatat ttgcgactct tctggcatgt aatatttcgt taaatatgaa      60
gtgctccatt tttattaact ttaaataatt ggttgtacga tcactttctt atcaagcgtt     120
actaaaatgc gtcaatctct ttgttcttcc atattcatat gtcaaaatct atcaaaattc     180
ttatatatct ttttcgaatt tgaagtgaaa tttcgataat ttaaaattaa atagaacata     240
tcattattta ggtgtcatat tgattttttat acttaattac taaatttggt taactttgaa    300
agtgtacatc aacgaaaaat tagtcaaacg actaaaataa ataaatatca tgtgttatta    360
agaaaattct cctataagaa tatttttaata gatcatatgt ttgtaaaaaa aattaatttt    420
tactaacaca tatatttact tatcaaaaat ttgacaaagt aagattaaaa taatattcat    480
ctaacaaaaa aaaaccagaa aatgctgaaa acccggcaaa accgaaccaa tccaaaccga    540
tatagttggt ttggtttgat tttgatataa accgaaccaa ctcggtccat ttgcacccct    600
aatcataata gctttaatat ttcaagatat tattaagtta acgttgtcaa tatcctggaa    660
attttgcaaa atgaatcaag cctatatggc tgtaatatga atttaaaagc agctcgatgt    720
ggtggtaata tgtaatttac ttgattctaa aaaaatatcc caagtattaa taatttctgc    780
taggaagaag gttagctacg atttacagca aagccagaat acaaagaacc ataaagtgat    840
tgaagctcga aatatacgaa ggaacaaata ttttttaaaaa aatacgcaat gacttggaac    900
aaaagaaagt gatatatttt ttgttcttaa acaagcatcc cctctaaaga atggcagttt    960
tcctttgcat gtaactatta tgctcccttc gttacaaaaa ttttggacta ctattgggcg   1020
cggggcgcgc ccggtccaaa gaccagaggg ctattgagac ttttcaacaa agggtaatat   1080
cgggaaacct cctcggattc cattgcccag ctatctgtca cttcatcgaa aggacagtag   1140
aaaaggaaga tggcttctac aaatgccatc attgcgataa aggaaaggct atcgttcaag   1200
atgcctctac cgacagtggt cccaaagatg acccccacc cacgaggaac atcgtggaaa   1260
aagaagacgt tccaaccacg tcttcaaagc aagtggattg atgtgataca tggtggagca   1320
cgacactctc gtctactcca agaatatcaa agatacagtc tcagaagacc agagggctat   1380
tgagactttt caacaaaggg taatatcggg aaacctcctc ggattccatt gcccagctat   1440
ctgtcacttc atcgaaagga cagtagaaaa ggaagatggc ttctacaaat gccatcattg   1500
cgataaagga aaggctatcg ttcaagatgc ctctaccgac agtggtccca agatggacc   1560
cccacccacg aggaacatcg tggaaaaaga agacgttcca accacgtctt caaagcaagt   1620
ggattgatgt gatatctcca ctgacgtaag ggatgacgca caatcccact atccttcgca   1680
agacccttcc tctatataag gaagttcatt tcatttggag aggacacgct gaattcacta   1740
cacagattag attcatcgaa agattcatca agaagaagaa aactatggag tcaagcgtta   1800
agccaaaccc attcctctca ttttcttctt ttattcatca ccaatgtact agattcagta   1860
gcgatttgag tgctagaatc gaagatacaa agaggtttgc tgagactctt gcaacaagaa   1920
ggttttcttt gcctactcca cctccattcg cttccgtttc catggggtgt atctataagt   1980
tcggtactag cccagattcc aaagcaacag tgtctggaga tcattgggat cacggactta   2040
atggtgaaaa ctgggaggga aaagatggag ctggtaatgc atgggtgtgc aagacaggta   2100
gaaagcaatc accaattaat gttccacaat atcaggtgtt ggatgaaag ggttcaaaaa    2160
ttgctaatgg tcttcaaact cagtggagtt accctgattt gatgtctaac ggaacatcag   2220
```

```
ttcaagttat taataacgga catactatac aagttcagtg gacatacaac tacgctggtc    2280
atgcaactat tgctatccca gcaatgcaca atcaaacaaa caggattgtt gatgtgcttg    2340
aaatgagacc taatgatgct gcagataggg ttactgctgt gccaacacag tttcacttcc    2400
attcaactag tgaacatctt ttggcaggaa agatctatcc tttagagctc catatagttc    2460
accaagtgac tgaaaagctt gaggcttgta aaggaggttg ctttagtgtt acaggaatcc    2520
ttttccagtt ggataatggt ccagataacg aactccttga acctatattc gctaatatgc    2580
caagtagaga aggtactttc agcaacttac ctgcaggaac tacaattaag ctcggagagc    2640
ttttgccatc tgatagggat tatgttactt acgaaggatc tcttactaca cctccatgtt    2700
ctgagggttt actctggcat gtgatgacac aacctcagag aatttctttt ggacagtgga    2760
atagatacag attagctgtt ggtctcaaag aatgcaactc aactgagaca gctgcagatg    2820
ctggacatca ccatcaccat agaaggcttt tgcacaatca tgcacactta aagagggttc    2880
ctgctgcaac tagcgaacca aagcattatt ttagaagagt tatgcttgct gagtctgcaa    2940
atccagatgc atacacatgc aaagctgttg cattcggtca aaactttagg aaccctcagt    3000
atgctaacgg aagaactatc aagctcgcta ggtatcataa acatctgaaa gattgggaac    3060
atctggaaga atttgcggcc gctcatcacc atcaccatca ctagctcgag ctcggatcct    3120
ctagagtccg caaaaatcac cagtctctct ctacaaatct atctctctct attttctcc     3180 agaataatgt gtgagtagtt cccagataag ggaattaggg ttcttatagg gtttcgctca    3240
tgtgttgagc atataagaaa cccttagtat gtatttgtat ttgtaaaata cttctatcaa    3300
taaaatttct aattcctaaa accaaaatcc agtgaccggg cggccggccg ccctagaaa     3360 tatttgcgac tcttctggca tgtaatattt cgttaaatat gaagtgctcc attttattta    3420
actttaaata attggttgta cgatcacttt cttatcaagc gttactaaaa tgcgtcaatc    3480
tctttgttct tccatattca tatgtcaaaa tctatcaaaa ttcttatata tcttttttcga    3540 atttgaagtg aaatttcgat aatttaaaat taaatagaac atatcattat ttaggtgtca    3600
tattgatttt tatacttaat tactaaattt ggttaacttt gaaagtgtac atcaacgaaa    3660
aattagtcaa acgactaaaa taaataaata tcatgtgtta ttaagaaaat tctcctataa    3720
gaatatttta atagatcata tgtttgtaaa aaaaattaat ttttactaac acatatattt    3780
acttatcaaa aatttgacaa agtaagatta aaataatatt catctaacaa aaaaaaacca    3840
gaaaatgctg aaaacccggc aaaaccgaac caatccaaac cgatatagtt ggtttggttt    3900
gattttgata taaaccgaac caactcggtc catttgcacc cctaatcata atagctttaa    3960
tatttcaaga tattattaag ttaacgttgt caatatcctg gaaattttgc aaaatgaatc    4020
aagcctatat ggctgtaata tgaatttaaa agcagctcga tgtggtggta atatgtaatt    4080
tacttgattc taaaaaaata tcccaagtat taataatttc tgctaggaag aaggttagct    4140
acgatttaca gcaaagccag aatacaaaga accataaagt gattgaagct cgaaatatac    4200
gaaggaacaa atatttttaa aaaaatacgc aatgacttgg aacaaaagaa agtgatatat    4260
tttttgttct taaacaagca tcccctctaa agaatggcag ttttcctttg catgtaacta    4320
ttatgctccc ttcgttacaa aaattttgga ctactattgg gcgggtggag ggggatcaga    4380
ttgtcgtttc ccgccttcag tttaaactat cagtgtttga caggatatat tggcgggtaa    4440
acctaagaga aaagagcgtt tattagaata atcggatatt taaagggcg tgaaaaggtt     4500 tatccgttcg tccatttgta tgtgtacatc accgacgagc aaggcaagac cgagcgcctt    4560
```

```
tccgacgctc accgggctgg ttgccctcgc cgctgggctg gcggccgtct atggccctgc    4620
aaacgcgcca gaaacgccgt cgaagccgtg tgcgagacac cggccgccgg cgttgtggat    4680
acctcgcgga aaacttggcc ctcactgaca gatgaggggc ggacgttgac acttgagggg    4740
ccgactcacc cggcgcggcg ttgacagatg aggggcaggc tcgatttcgg ccggcgacgt    4800
ggagctggcc agcctcgcaa atcggcgaaa acgcctgatt ttacgcgagt ttcccacaga    4860
tgatgtggac aagcctgggg ataagtgccc tgcggtattg acacttgagg ggcgcgacta    4920
ctgacagatg aggggcgcga tccttgacac ttgagggggca gagtgctgac agatgagggg    4980
cgcacctatt gacatttgag gggctgtcca caggcagaaa atccagcatt tgcaagggtt    5040
tccgcccgtt tttcggccac cgctaacctg tcttttaacc tgcttttaaa ccaatattta    5100
taaaccttgt ttttaaccag ggctgcgccc tgtgcgcgtg accgcgcacg ccgaaggggg    5160
gtgccccccc ttctcgaacc ctcccggccc gctaacgcgg gcctcccatc cccccagggg    5220
ctgcgcccct cggccgcgaa cggcctcacc ccaaaaatgg cagcgctggc agtccttgcc    5280
attgccggga tcggggcagt aacgggatgg gcgatcagcc cgacaagcta cccctatttg    5340
tttatttttc taaatacatt caaatatgta tccgctcatg agacaataac cctgataaat    5400
gcttcaataa tattgaaaaa ggaagagtat gagtattcaa catttccgtg tcgcccttat    5460
tccctttttt gcggcatttt gccttcctgt tttgctcac ccagaaacgc tggtgaaagt    5520
aaaagatgct gaagatcagt tgggtgcacg agtgggttac atcgaactgg atctcaacag    5580
cggtaagatc cttgagagtt ttcgccccga agaacgtttt ccaatgatga gcacttttaa    5640
agttctgcta tgtggcgcgg tattatcccg tattgacgcc gggcaagagc aactcggtcg    5700
ccgcatacac tattctcaga atgacttggt tgagtactca ccagtcacag aaaagcatct    5760
tacggatggc atgacagtaa gagaattatg cagtgctgcc ataaccatga gtgataacac    5820
tgcggccaac ttacttctga acgatcgg aggaccgaag gagctaaccg cttttttgca    5880
caacatgggg gatcatgtaa ctcgccttga tcgttgggaa ccggagctga atgaagccat    5940
accaaacgac gagcgtgaca ccacgatgcc tgtagcaatg gcaacaacgt tgcgcaaact    6000
attaactggc gaactactta ctctagcttc ccggcaacaa ttaatagact ggatggaggc    6060
ggataaagtt gcaggaccac ttctgcgctc ggcccttccg gctggctggt ttattgctga    6120
taaatctgga gccggtgagc gtgggtctcg cggtatcatt gcagcactgg ggccagatgg    6180
taagccctcc cgtatcgtag ttatctacac gacggggagt caggcaacta tggatgaacg    6240
aaatagacag atcgctgaga taggtgcctc actgattaag cattggtaac tgtcagacca    6300
agtttactca tatatacttt agattgattt aaaacttcat ttttaattta aaaggatcta    6360
ggtgaagatc cttttttgata atctcatgac caaaatccct taacgtgagt tttcgttcca    6420
ctgagcgtca gaccccgtag aaaagatcaa aggatcttct tgagatcctt ttttctgcg    6480
cgtaatctgc tgcttgcaaa caaaaaaacc accgctacca gcggtggttt gtttgccgga    6540
tcaagagcta ccaactcttt ttccgaaggt aactggcttc agcagagcgc agataccaaa    6600
tactgtcctt ctagtgtagc cgtagttagg ccaccacttc aagaactctg tagcaccgcc    6660
tacatacctc gctctgctaa tcctgttacc agtggctgct gccagtggcg ataagtcgtg    6720
tcttaccggg ttggactcaa gacgatagtt accggataag gcgcagcggt cgggctgaac    6780
ggggggttcg tgcacacagc ccagcttgga gcgaacgacc tacaccgaac tgagatacct    6840
acagcgtgag ctatgagaaa gcgccacgct tcccgaaggg agaaaggcgg acaggtatcc    6900
ggtaagcggc agggtcggaa caggagagcg cacgagggag cttccagggg gaaacgcctg    6960
```

```
gtatctttat agtcctgtcg ggtttcgcca cctctgactt gagcgtcgat ttttgtgatg    7020
ctcgtcaggg gggcggagcc tatggaaaaa cgccagcaac gcggccttt tacggttcct     7080
ggccttttgc tggccttttg ctcacatgga ctctagctag aggatcacag gcagcaacgc    7140
tctgtcatcg ttacaatcaa catgctaccc tccgcgagat catccgtgtt tcaaacccgg    7200
cagcttagtt gccgttcttc cgaatagcat cggtaacatg agcaaagtct gccgccttac    7260
aacggctctc ccgctgacgc cgtcccggac tgatgggctg cctgtatcga gtggtgattt    7320
tgtgccgagc tgccggtcgg ggagctgttg gctggctggt ggcaggatat attgtggtgt    7380
aaacaaattg acgcttagac aacttaataa cacattgcgg acgttttaa tgatcgaata     7440
ctaacgtctc taccagatat cagcttgcat gccggtcgat ctagtaacat agatgacacc    7500
gcgcgcgata atttatccta gtttgcgcgc tatattttgt tttctatcgc gtattaaatg    7560
tataattgcg ggactctaat cataaaaacc catctcataa ataacgtcat gcattacatg    7620
ttaattatta catgcttaac gtaattcaac agaaattata tgataatcat cgcaagaccg    7680
gcaacaggat tcaatcttaa gaaactttat tgccaaatgt ttgaacgatc tgcttgactc    7740
tagctagagt ccgaacccca gagtcccgct cagaagaact cgtcaagaag gcgatagaag    7800
gcgatgcgct gcgaatcggg agcggcgata ccgtaaagca cgaggaagcg gtcagcccat    7860
tcgccgccaa gctcttcagc aatatcacgg gtagccaacg ctatgtcctg atagcggtcc    7920
gccacaccca gccggccaca gtcgatgaat ccagaaaagc ggccatttc caccatgata    7980
ttcggcaagc aggcatcgcc ctgggtcacg acgagatcct cgccgtcggg catccgcgcc    8040
ttgagcctgg cgaacagttc ggctggcgcg agccctgat gctcttcgtc cagatcatcc    8100
tgatcgacaa gaccggcttc catccgagta cgtcctcgct cgatgcgatg tttcgcttgg    8160
tggtcgaatg ggcaggtagc cggatcaagc gtatgcagcc gccgcattgc atcagccatg    8220
atggatactt tctcggcagg agcaaggtga gatgacagga gatcctgccc cggcacttcg    8280
cccaatagca gccagtccct tcccgcttca gtgacaacgt cgagcacagc tgcgcaagga    8340
acgcccgtcg tggccagcca cgatagccgc gctgcctcgt cttggagttc attcagggca    8400
ccggacaggt cggtcttgac aaaaagaacc gggcgcccct gcgctgacag ccggaacacg    8460
gcggcatcag agcagccgat tgtctgttgt gcccagtcat agccgaatag cctctccacc    8520
caagcggccg gagaacctgc gtgcaatcca tcttgttcaa tcatgcctcg atcgagttga    8580
gagtgaatat gagactctaa ttggataccg aggggaattt atggaacgtc agtggagcat    8640
ttttgacaag aaatatttgc tagctgatag tgaccttagg cgactttga acgcgcaata     8700
atggtttctg acgtatgtgc ttagctcatt aaactccaga aacccgcggc tgagtggctc    8760
cttcaacgtt gcggttctgt cagttccaaa cgtaaacgg cttgtcccgc gtcatcggcg     8820
ggggtcataa cgtgactccc ttaattctcc gctcatgatc gatatccatt gaagagcaag    8880
ct                                                                   8882
```

GENETICALLY MODIFIED HIGHER PLANTS WITH INCREASED PHOTOSYNTHESIS AND/OR BIOMASS PRODUCTION, METHODS AND USES THEREOF

CROSS REFERENCE TO RELATED APPLICATIONS

This is a US national phase application under 35 USC § 371 of international patent application no. PCT/EP2015/077803, filed Nov. 26, 2015, which itself claims priority to European application no. EP 14195613.6, filed Dec. 1, 2014. Each of the applications referred to in this paragraph are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing with file "PCTEP2015077803_SEQ_ID" created on 10 May 2017, filed on 31 May 2017 and having a size of 18 Kilobytes. The sequence listing contained in this ASCII formatted document forms part of the specification and is herein incorporated by reference in its entirety.

FIELD OF THE INVENTION

The technology provided herein generally relates relates to genetically modified higher plants, for example C3 and C4 plants, and subsequent generations thereof, comprising stable and/or transient expression of at least one gene-product (e.g. mRNA or protein) of the "*Chlamydomonas reinhardtii* $CO_2$ concentrating mechanism" (CCM), wherein the expression takes place in the intermembrane space and/or one or more subcellular compartments of the chloroplasts of the higher plant, and wherein this expression increases one or more of the characteristics selected from the group of photosynthetic rate, photosynthetic carbon fixation, chlorophyll level and/or biomass of the genetically modified higher plant (T0) and/or of the $T_1$ and/or $T_2$ generation or any subsequent plant generation of said genetically modified higher plant.

In one aspect the present invention relates to higher plants comprising expression of *Chlamydomonas* bicarbonate transporters (LCIA, LCIB) and carbonic anhydrases (CAH1, CAH3) alone or in combination in different subcellular compartments of the chloroplasts of the C3- or C4 plant.

In some aspects the LCIA, LCIB, CAH1 and CAH3 are expressed in typical localizations of the genetically modified higher plant, in other aspects they are expressed in atypical localizations of the genetically modified higher plant.

In general the present invention pertains to improved cereals, legumes, fruits, roots and tubers, oil crops, fibre crops and trees.

Furthermore, the present invention relates to methods and uses of such genetically modified higher plants.

BACKGROUND

C3 carbon fixation is one of three metabolic pathways for carbon fixation in photosynthesis, along with C4 and CAM.

In the C3 process carbon dioxide and ribulose bisphosphate (RuBP, a 5-carbon sugar) are converted into 3-phosphoglycerate through the following reaction:

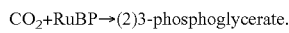

The C3 plants, originating during Mesozoic and Paleozoic eras, predate the C4 plants and still represent approximately 95% of Earth's plant biomass. C3 plants lose 97% of the water taken up through their roots to transpiration Plants that survive solely on C3 fixation (C3 plants) tend to thrive in areas where sunlight intensity is moderate, temperatures are moderate, carbon dioxide concentrations are around 200 ppm or higher, and ground water is plentiful.

Examples for C3-plants include rice, wheat, orange tree, wine plant, coffee plant, tobacco plant, tea plant, peanut plant, lemon tree, potato, carrot, tomato, peach tree, apple tree, pear tree, mango tree and barley.

Further examples include oats, rye, triticale, dry bean, soybean, mung bean, faba bean, cowpea, common pea, chickpea, pigeon pea, lentil, banana, coconut, taro, yams, sweet potato, cassava, sugar beet, cotton, jute, sisal, sesame, sunflower, rapeseed and safflower.

C3 plants have disadvantages to grow in hot areas because the enzyme Ribulose-1,5-bisphosphate-carboxylase/-oxygenase (RuBisCO) incorporates more oxygen into RuBP as temperature increases. This leads to increased photorespiration, which leads to a net loss of carbon and nitrogen from the plant and can, therefore, limit growth. In dry areas, C3 plants shut their stomata to reduce water loss, but this stops $CO_2$ from entering the leaves and, therefore, reduces the concentrating of $CO_2$ in the leaves. This lowers the $CO_2:O_2$ ratio and, therefore, also increases photorespiration.

C4 and CAM plants, on the other side, have adaptations that allow them to survive in hot and dry areas, and they can, therefore, out-compete C3 plants.

C4 carbon fixation is one of three biochemical mechanisms, along with C3 and CAM photosynthesis, used in carbon fixation. It is named for the 4-carbon molecule present in the first product of carbon fixation in the small subset of plants known as C4 plants, in contrast to the 3-carbon molecule products in C3 plants.

C4 fixation is an elaboration of the more common C3 carbon fixation and is believed to have evolved more recently. C4 and CAM overcome the tendency of the enzyme RuBisCO to wastefully fix oxygen rather than carbon dioxide in what is called photorespiration. This is achieved by using a more efficient enzyme to fix $CO_2$ in mesophyll cells and shuttling this fixed carbon via malate or aspartate to bundle-sheath cells. In these bundle-sheath cells, RuBisCO is isolated from atmospheric oxygen and saturated with the $CO_2$ released by decarboxylation of the malate or oxaloacetate. These additional steps, however, require more energy in the form of ATP. Because of this extra energy requirement, C4 plants are able to more efficiently fix carbon in only certain conditions, with the more common C3 pathway being more efficient in other conditions.

However, also C4 can be modified according to the present invention in order to improve the carbon fixation even further.

Examples for C4 plants include crab grass, corn (maize), amaranth, sorghum, millet, sugarcane, nut grass, crab grass, barnyard grass, fourwinged salt bush and chenopods.

*Chlamydomonas* is a genus of green algae consisting of unicellular flagellates, found in stagnant water and on damp soil, in freshwater, seawater, and even in snow as "snow algae".

*Chlamydomonas* is used as a model organism for molecular biology, especially studies of flagellar motility and chloroplast dynamics, biogenesis, and genetics.

Aquatic photosynthetic organisms, such as *Chlamydomonas reinhardtii*, can modulate their photosynthesis to acclimate to $CO_2$-limiting stress by inducing a carbon-concentrating mechanism (CCM) that includes carbonic anhydrases (CAH) and inorganic carbon (Ci) transporters.

The carbon-concentrating mechanism (CCM) allows *C. reinhardtii* to optimize carbon acquisition for photosynthesis. The CCM function to facilitate $CO_2$ assimilation, when inorganic carbon (Ci; $CO_2$ and/or $HCO_3^-$) is limited. By active Ci uptake systems, internal Ci levels are increased and then carbonic anhydrase supplies sufficient $CO_2$ to ribulose 1,5-bisphosphate carboxylase/oxygenase ("RuBisCO") by the dehydration of accumulated bicarbonate.

In the present invention newly identified components of the CCM are integrated into higher plants in order to increase one or more of the characteristics selected from the group of photosynthetic rate, photosynthetic carbon fixation, chlorophyll level and/or biomass of subsequent plant generations, especially the $T_1$ and/or $T_2$ generation, and any further generation of said genetically modified higher plant.

By this modification the higher plant may not only grow better and become more competitive in known habitats, but may even thrive in climatic conditions traditionally not occupied by this plant.

Further examples for higher plants include cereals, legumes, fruits, roots and tubers, oil crops, fibre crops and trees.

SUMMARY OF THE INVENTION

One aspect of the present invention relates to a genetically modified higher plant, and subsequent generations thereof, comprising stable or transient expression of at least one gene-product of the "*Chlamydomonas reinhardtii* $CO_2$ concentrating mechanism" (CCM), wherein the expression takes place in the intermembrane space and/or in one or more subcellular compartments of the chloroplasts of the plant.

In one aspect this expression increases one or more of the characteristics selected from the group of photosynthetic rate, photosynthetic carbon fixation, chlorophyll level and/or biomass of the genetically modified higher plant ($T_0$) and/or of the $T_1$ and/or $T_2$ generation or any subsequent generation of said genetically modified higher plant.

In one aspect said genetically modified higher plant is a C3-plant, in another aspect said genetically modified higher plant is a C4-plant.

Another aspect relates to gene-products of the "*Chlamydomonas reinhardtii* $CO_2$ concentrating mechanism" (CCM) selected from the group consisting of bicarbonate transporter LCIA, bicarbonate transporter LCIB, carbonic anhydrases CAH1 and/or carbonic anhydrases CAH3 of *Chlamydomonas reinhardtii*.

In even another aspect the expression of anyone of CAH1, CAH3, LCIA and LCIB results in faster growth and/or shorter vegetative phase in the $T_1$ generation of said genetically modified higher plant as compared to a wild type control.

In one aspect said gene-product of the "*Chlamydomonas reinhardtii* $CO_2$ concentrating mechanism" is carbonic anhydrase CAH1 of *Chlamydomonas reinhardtii*.

In another aspect said carbonic anhydrase CAH1 is expressed in the atypical localization intermembrane space of the chloroplast of the genetically modified higher plant.

It is one aspect of the present invention that expression in atypical compartments of the chloroplast, such as for example the atypical expression of CAH1 as shown in the examples, increases one or more of the characteristics selected from the group of photosynthetic rate, photosynthetic carbon fixation, chlorophyll level and/or biomass of the genetically modified higher plant ($T_0$) and/or of the $T_1$ and/or $T_2$ generation or any subsequent generation of said genetically modified higher plant.

It yet another aspect of the present invention expression in typical compartments of the chloroplast increases one or more of the characteristics selected from the group of photosynthetic rate, photosynthetic carbon fixation, chlorophyll level and/or biomass of the genetically modified higher plant ($T_0$) and/or of the $T_1$ and/or $T_2$ generation or any subsequent generation of said genetically modified higher plant.

In yet another aspect of the present invention the expression of said carbonic anhydrase CAH1 in the intermembrane space of the chloroplast of the genetically modified higher plant increases the photosynthetic rates by at least 8%, the levels of chlorophyll by at least 7% and/or the biomass by at least 22%, as compared to a wild type control, in the $T_1$ and/or $T_2$ generation or any subsequent generation of said transgenic genetically modified higher plant. Also the leaf number is increased in those plants.

In one aspect of the present invention at the end of vegetative period of the CAH1 $T_2$-plant, three parameters defining biomass are increased as compared to wild-type control:
Leaf area: +22%
Fresh weight: +26%
Dry weight: +29%

In yet another aspect of the present invention the percentage increase at week 3 and at the end of vegetative period of the CAH1 $T_2$-plant is as follows as compared to wild-type control (percentage increase at week 3/percentage increase at end of veg. period; nd: not determined):
Leaf area: +142%/+22%
Chlorophyll content: +15%/+13%
Leaf number: +21%/+24%
Fresh weight: +nd/+26%
Dry weight: +nd/+29

In a further aspect of the present invention said gene-product of the "*Chlamydomonas reinhardtii* $CO_2$ concentrating mechanism" (CCM) is carbonic anhydrase CAH3 of *Chlamydomonas reinhardtii*.

In another aspect of the present invention said carbonic anhydrase CAH3 is expressed in the thylakoid lumen of the chloroplast of the genetically modified higher plant.

In yet another aspect of the present invention said carbonic anhydrase CAH3 expressed in the thylakoid lumen of the chloroplast of the genetically modified higher plant increases the photosynthetic rates by at least 8%, the levels of chlorophyll by at least 10%, the stomata size is increased by up to 50% and/or the biomass by at least 31% as compared to a wild type control, in the $T_1$ and/or $T_2$ generation or any subsequent generation of said transgenic genetically modified higher plant as compared to wild-type control.

In one aspect of the present invention at the end of vegetative period of the CAH3 $T_2$-plant, three parameters defining biomass are increased as compared to wild-type control:
Leaf area: +24%
Fresh weight: +34%
Dry weight: +31%

In yet another aspect of the present invention the percentage increase at week 3 and at the end of vegetative period of the CAH3 $T_2$-plant is as follows as compared to wild-type control (percentage increase at week 3/percentage increase at end of veg. period; nd: not determined):
  Leaf area: +78%/+24%
  Chlorophyll content: +11%/+10%
  Leaf number: +26%/+64%
  Fresh weight: +nd/+34%
  Dry weight: +nd/+31%

In a further aspect of the present invention said gene-product of the "*Chlamydomonas reinhardtii* $CO_2$ concentrating mechanism" (CCM) is bicarbonate transporter LCIA of *Chlamydomonas reinhardtii*.

In another aspect of the present invention said bicarbonate transporter LCIA is expressed in the inner envelope of the chloroplast of the genetically modified higher plant.

In yet another aspect of the present invention the expression of said bicarbonate transporter LCIA in the inner envelope of the chloroplast of the genetically modified higher plant increases the photosynthetic rates by at least 8%, the levels of chlorophyll by at least 15% and/or biomass by at least 33% at the end of the vegetative period, as compared to a wild type control, in the $T_1$ and/or $T_2$ generation or any subsequent generation of said transgenic genetically modified higher plant.

In one aspect of the present invention at the end of vegetative period of the LCIA $T_2$-plant, three parameters defining biomass are increased as compared to wild-type control:
  Leaf area: +33%
  Fresh weight: +54%
  Dry weight: +41%

In yet another aspect of the present invention the percentage increase at week 3 and at the end of vegetative period of the LCIA $T_2$-plant is as follows as compared to wild-type control (percentage increase at week 3/percentage increase at end of veg. period; nd: not determined):
  Leaf area: +93%/+33%
  Chlorophyll content: +11%/+16%
  Leaf number: +17%/+19%
  Fresh weight: +nd/+54%
  Dry weight: nd/+41%

In a further aspect of the present invention said gene-product of the "*Chlamydomonas reinhardtii* $CO_2$ concentrating mechanism" (CCM) is bicarbonate transporter LCIB of *Chlamydomonas reinhardtii*.

In yet another aspect of the present invention said bicarbonate transporter LCIB is expressed in the stroma of the chloroplast of the genetically modified higher plant.

In yet another aspect of the present invention the expression of said bicarbonate transporter LCIB in the stroma of the chloroplast of the genetically modified higher plant increases the biomass, as compared to a wild type control, in the $T_1$ and/or $T_2$ generation or any subsequent generation of said transgenic genetically modified higher plant.

In one aspect of the present invention at the end of vegetative period of the LCIB $T_2$-plant, three parameters defining biomass are increased as compared to wild-type control:
  Leaf area: +23%
  Fresh weight: +30%
  Dry weight: +28%

In yet another aspect of the present invention the percentage increase at week 3 and at the end of vegetative period of the LCIB $T_2$-plant is as follows as compared to wild-type control (percentage increase at week 3/percentage increase at end of veg. period; nd: not determined):
  Leaf area: +78%/+23%
  Chlorophyll content: +10%/+15%
  Leaf number: +27%/+24%
  Fresh weight: +nd/+30%
  Dry weight: +nd/+28%

One aspect of the present invention also relates to methods for producing a genetically modified higher plant.

One aspect of the present invention also relates to uses of the genetically modified genetically modified higher plant which are modified in order to increase the production rate of a natural and/or transgenic product produced by said genetically modified higher plant as compared to the wild type control.

Another aspect of the present invention is the use wherein the natural product produced by the genetically modified higher plant is selected from a flower, a fruit, a seed, a nut, a leave, a stem and/or any other commercially applicable part of the plant.

Yet another aspect of the present invention is the use wherein the transgenic product produced by the genetically modified higher plant is selected from a nucleic acid, a protein, a peptide and/or any other metabolic product produced with transgenic means.

In one aspect of the present invention the above mentioned genetically modified higher plant are a C3-plant, in another aspect said genetically modified higher plant is a C4-plant.

Yet another aspect of the present invention is the use of the inventive methods in order to increase one or more of the characteristics selected from the group of photosynthetic rate, photosynthetic carbon fixation, chlorophyll level and/or biomass in the $T_1$ and/or $T_2$ and/or in any subsequent generation of a genetically modified higher plant, either a C3-plant or a C4-plant.

Yet another aspect of the present invention is the use of the inventive methods in order to create a genetically modified higher plant which is able to grow under climate and/or nutritional conditions which do not allow the growth of a wild type control or only with reduced efficiency.

In some aspects of the invention the C3-plant belongs to the class of Dicotyledons, in other aspects to the order of Solanales, in yet other aspects to the family of Solanaceae, in yet other aspects to the genus *Nicotiana*, in yet other aspects the C3-plant is a tobacco plant (*Nicotiana tabacum*).

In some aspects of the invention uses are disclosed for the increase of one or more of the characteristics selected from the group of photosynthetic rate, photosynthetic carbon fixation, chlorophyll level and/or biomass in the T1 and/or T2 and/or in any subsequent generation of a genetically modified higher plant.

In another aspect of the invention uses are disclosed in order to create a genetically modified higher plant which is able to grow under climate and/or nutritional conditions which do not allow the growth of a wild-type control or the growth with lower efficiency.

In another aspect of the invention the genetically modified higher plant is selected from the group comprising rice, wheat, orange tree, wine plant, coffee plant, tobacco plant, tea plant, peanut plant, lemon tree, potato, carrot, tomato, peach tree, apple tree, pear tree, mango tree, barley, oats, rye, triticale, dry bean, soybean, mung bean, faba bean, cowpea, common pea, chickpea, pigeon pea, lentil, banana, coconut, taro, yams, sweet potato, cassava, sugar beet, cotton, jute, sisal, sesame, sunflower, rapeseed, safflower, crab grass, corn (maize), amaranth, sorghum, millet, sugarcane, nut grass, crab grass, barnyard grass, fourwinged salt bush and/or chenopods.

Before the disclosure is described in detail, it is to be understood that this disclosure is not limited to the particular aspects of the present disclosure. It is also to be understood that the terminology used herein is for purposes of describing particular aspects only, and is not intended to be limiting. It must be noted that, as used in the specification and the appended claims, the singular forms "a," "an" and "the" include singular and/or plural reference unless the context clearly dictates otherwise. It is moreover to be understood that, in case parameter ranges are given which are delimited by numeric values, the ranges are deemed to include these limitation values.

Transgenic tobacco producing CAH1, CAH3, LCIA or LCIB were generated. The localization of the different CCM-proteins in the cell compartments of a higher plant, e.g. tobacco plant, are depicted here. The abbreviation "BT" refers to endogenous tobacco bicarbonate transporters, the abbreviation "CA" to endogenous tobacco carbonic anhydrases. A: CAH1 is localized in intermembrane space (atypical localization). B: CAH3 is localized in the thylakoid lumen (typical or native localization). C: LCIA is localized in the inner membrane (typical or native localization). D: LCIB is localized in the stroma (typical or native localization).

Figure 3:
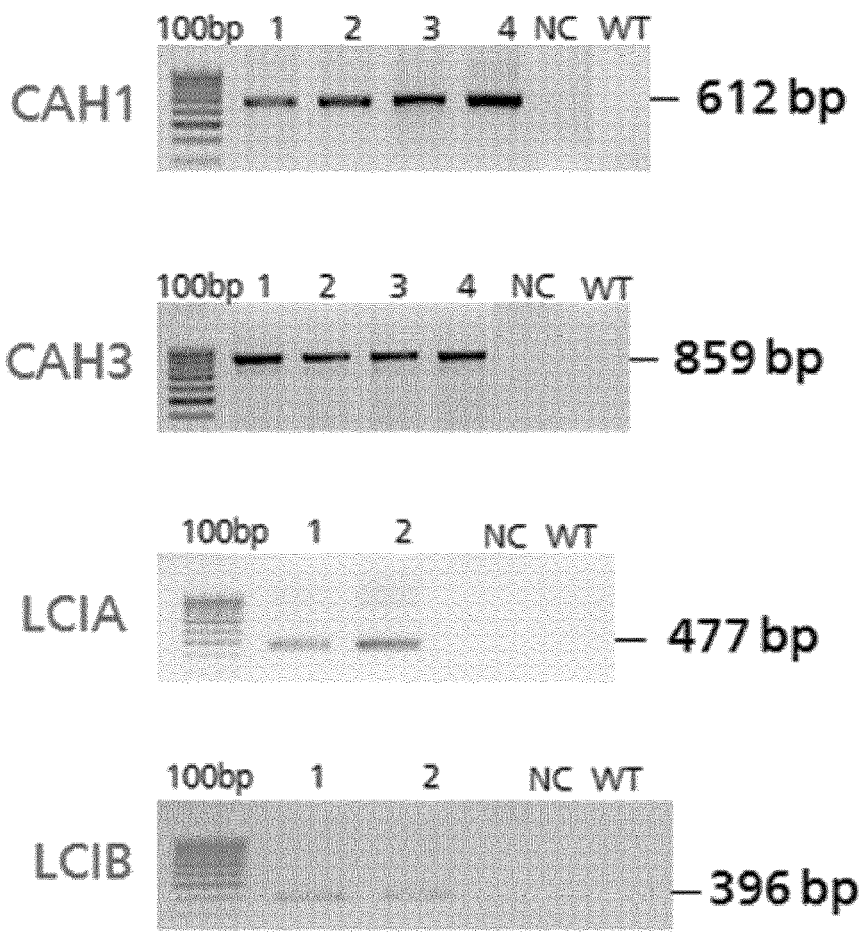

FIG. 3. Transcript-Characterization of transgenic $T_2$ plants

The RNA transcript presence was confirmed in $T_2$-plants by RT-PCR (reverse transcriptase PCR) with gene specific primers. Lines 1-4 refer to the transgenic lines for CAH1, CAH3, LCIA or LCIB. As control (WT) non-transgenic tobacco was used. NC is the negative control of RT-PCR. Columns 1-4 refer to the accumulation of the CAH1 or CAH3 transgene in four different CAH1 or CAH3 transgenic T2 lines, respectively; while columns 1-2 refer to the accumulation of the LCIA or LCIB transgene in LCIA or LCIB transgenic T2 lines, respectively.

Figure 4:
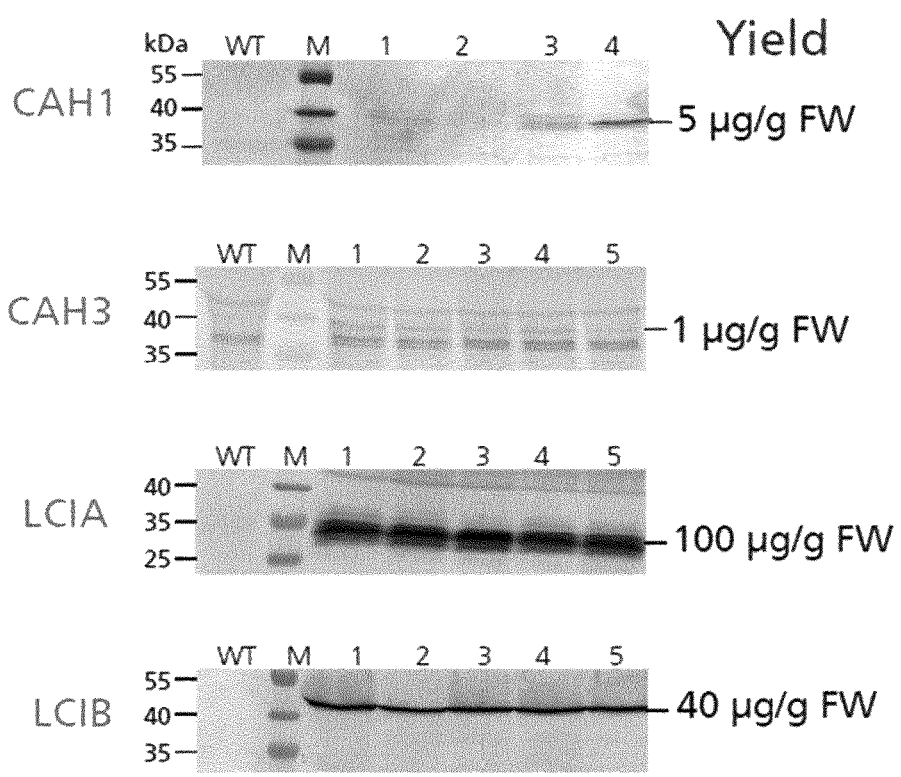

FIG. 4. Recombinant protein characterization of transgenic $T_2$ plants

The presence of recombinant protein was measured by immunoblot analysis. The yield of protein in μg/g is depicted on the right. "FW" means "fresh weight". Lines 1-4 refer to the transgenic lines for CAH1, CAH3, LCIA or LCIB. As control (WT) non-transgenic tobacco was used. CAH1, LCIA and LCIB were detected by Tag54-specific antibody. CAH3 was detected with a specific antibody for CAH3. Columns 1-4 and 1-5 refer to different transgenic plants.

Figure 5:
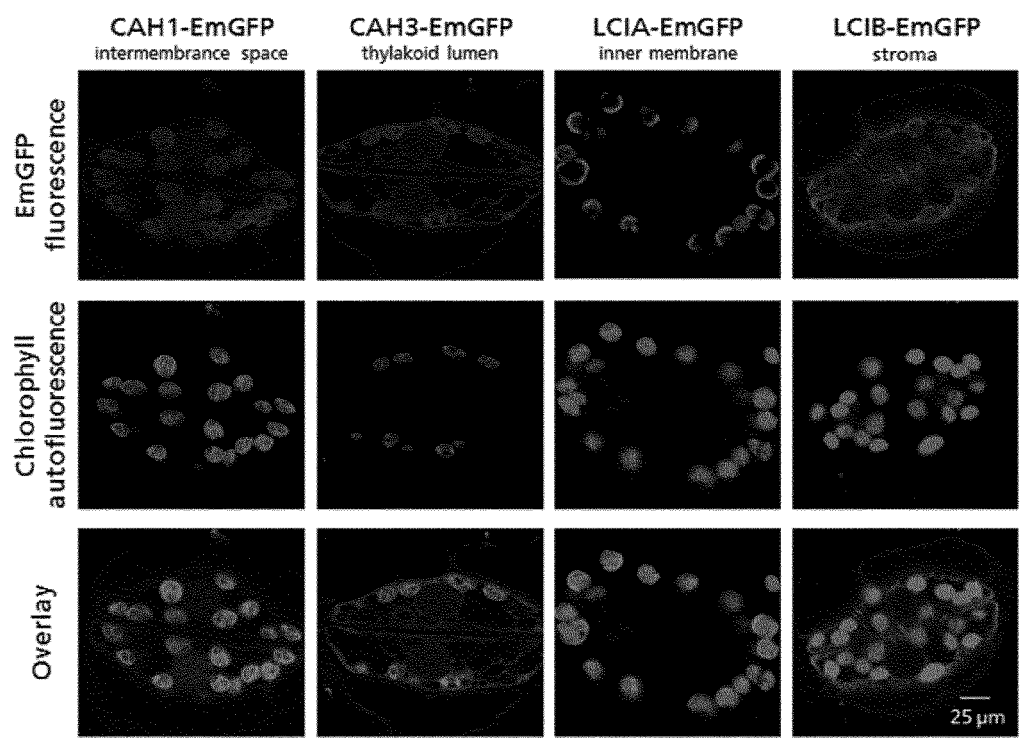

FIG. 5. Localization of recombinant proteins by confocal microscopy

FIG. 5 shows the correct localization of all EmGFP fusion proteins in tobacco chloroplasts of recombinant proteins within the genetically modified higher plant cell by confocal microscopy.

Figure 6:
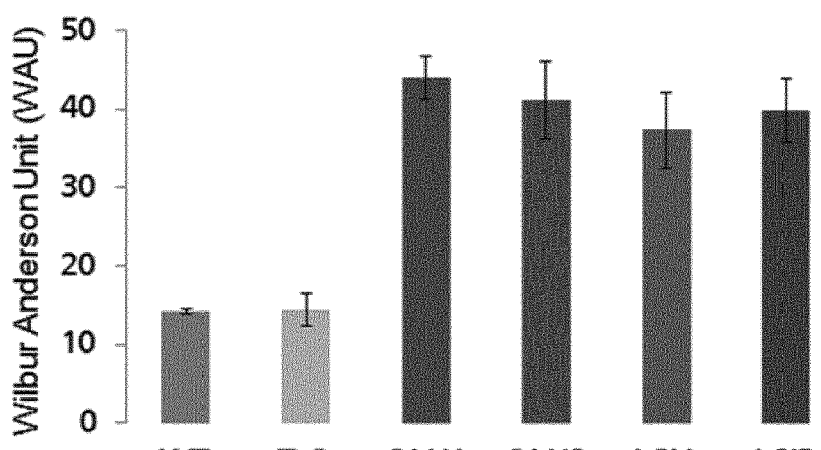

FIG. 6. Recombinant proteins are functional in $T_2$ tobacco chloroplasts

FIG. 6 shows that all recombinant proteins expressed in chloroplasts of the genetically higher plant, e.g. tobacco, were functional. The analysis was done by measuring the carbonic anhydrase (CA) activity analysis. The measurement took place in 5.5 week old plants, all values are mean values with a standard deviation (SD); number of plants per analysis (n=4). Plants producing CAH1 and CAH3 show CA activity in vitro. High CA activity in transgenic lines producing LCIA or LCIB bicarbonate transporters. LCIA and LCIB expression affects endogenous plant CA activity. The abbreviation "T.C." stands for "non-related transgenic control". "WT" means wild-type control (non-modified tobacco plant).

Figure 7:
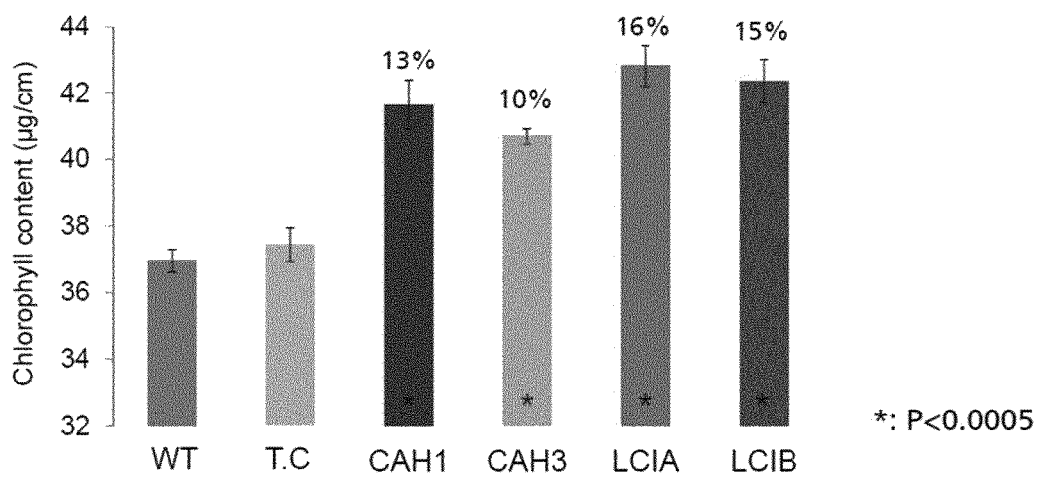

FIG. 7. Higher chlorophyll content in transgenic T2 lines

FIG. 7 shows the increased chlorophyll content in transgenic $T_2$ lines. 8.5 weeks old tobacco plants were measured with SPAD-502Plus®-device (Konica Minolta) in order to test the content of chlorophyll a+b. All transgenic lines have significant (p<0.0005) higher chlorophyll content as compared to wild type and non-related transgenic control. The abbreviation "T.C." stands for "non-related transgenic control". "WT" means wild-type control (non-modified tobacco plant).

FIG. 8. Enhanced growth of transgenic lines at early stages of development

FIG. 8, A: 3-weeks old plantlets (tobacco) in MS plates are depicted. +/− refers to presence or absence of kanamycin selection in MS plates. Shoot biomass, leaf number and total leaf area was increased in all transgenic plants as compared to wild-type control (WT). The abbreviation "T.C." stands for "non-related transgenic control".

FIG. 8, B: 4.5-weeks old plants in soil are depicted. Again shoot biomass, leaf number and total leaf area was increased in all transgenic plants as compared to wild-type control (WT)

FIG. 9. Enhanced growth of *N. tabacum* T2 transgenic lines

FIG. 9 A, depicts the enhanced growth of tobacco plants with transgenic CCM-proteins. Leaf area was measured weekly in 5 to 8 week old plants. Mean+/−standard deviation is depicted. Number of plants (n=6).

FIG. 9 B, depicts the enhanced growth of 8-weeks old tobacco plants with LCIA. The larger leave size can easily be spotted.

Figure 10:
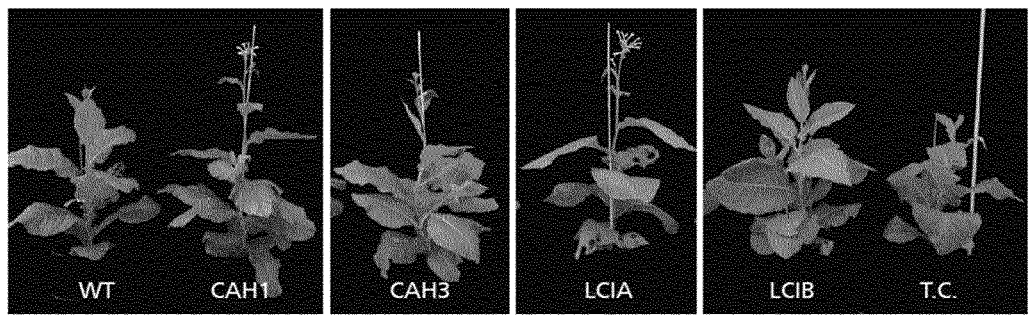

FIG. 10. Early-flowering phenotype of $T_2$ transgenic lines

FIG. 10 depicts the early-flowering phenotype of $T_2$ transgenic lines. The transgenic plants flower 1.5-2 weeks earlier than wild type and non-transgenic control. All plants are 8 weeks old of age.

Figure 11:
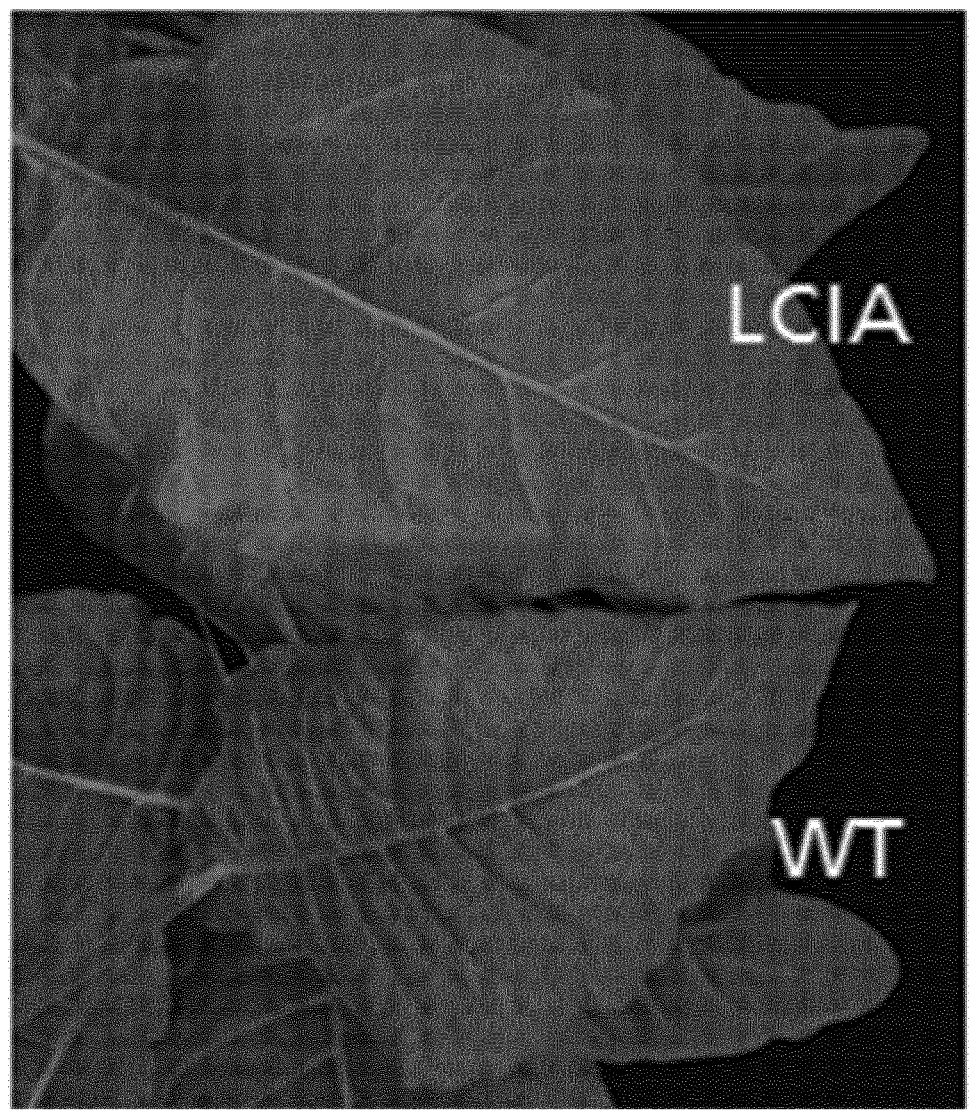

FIG. 11. Increase of leave size

FIG. 11 depicts the increase of leave size in 8 weeks old plants.

Figure 12:
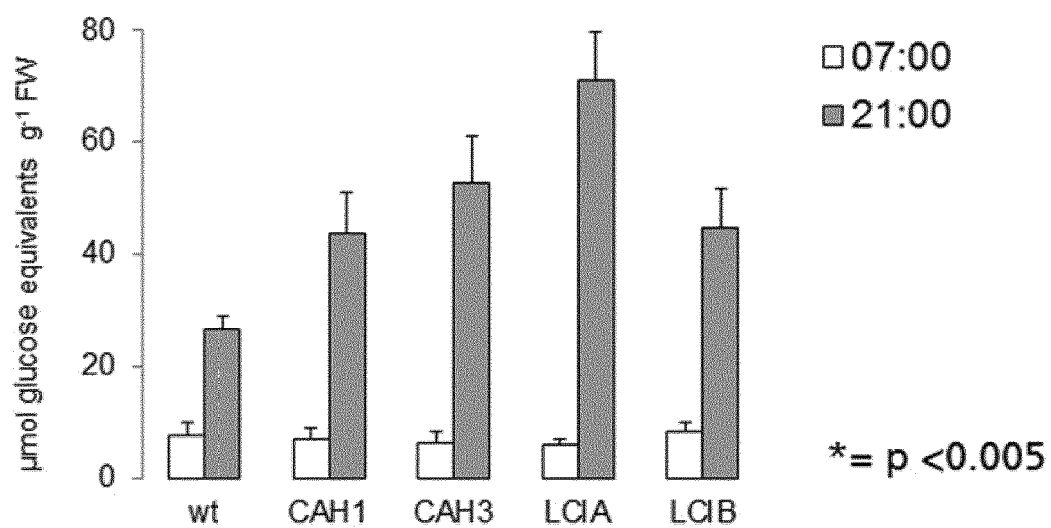

FIG. 12. Increased starch content in leaves of $T_2$ transgenic lines.

FIG. 12 depicts the significant increase of starch levels at the end of the illumination period in all transgenic lines compared to wild type. Starch analysis was measured in leaves of 6-weeks old plants.

FIG. 13. Enhanced photosynthesis in transgenic plants. Analyses were performed when plants were 7-8-weeks old. N WT=7; n CAH1=8; n CAH3=10; n LCIA=11; n LCIB=3.

FIG. 14. Nucleic acid sequence of CAH1 (SEQ ID NO. 1).

FIG. 15. Nucleic acid sequence of CAH3 (SEQ ID NO. 2).

FIG. 16. Nucleic acid sequence of LCIA (SEQ ID NO. 3).

FIG. 17. Nucleic acid sequence of LCIB (SEQ ID NO. 4).

Figure 18:
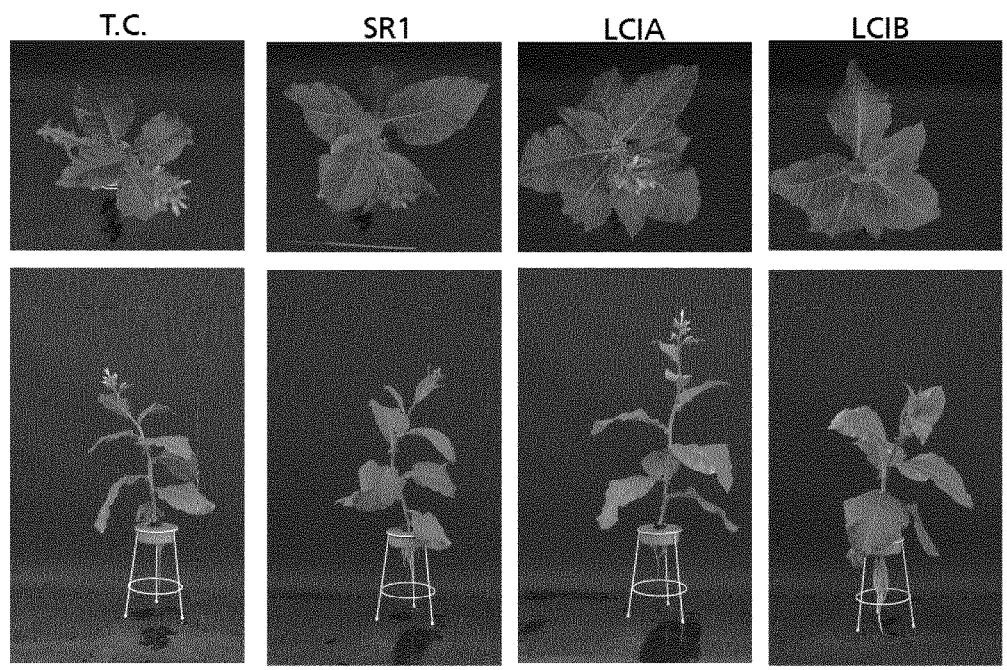

FIG. 18. Enhanced growth of $T_4$ transgenic lines grown in hydroponic cultures under nitrogen depletion (75% less nitrogen).

Figure 19:
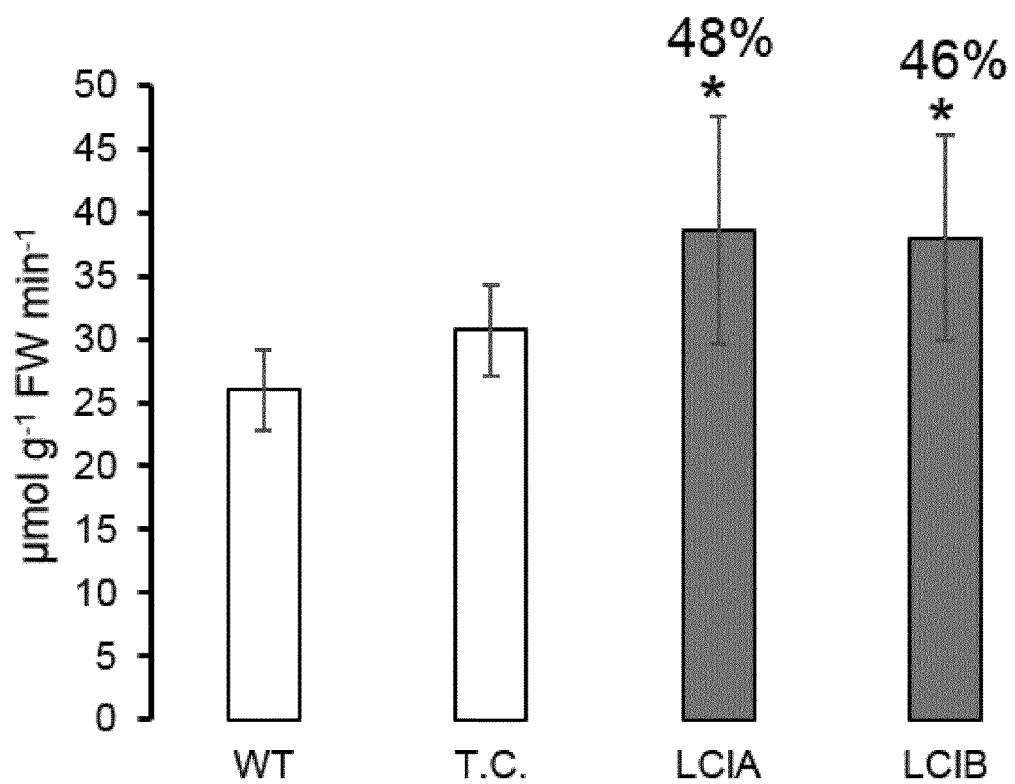

FIG. 19 depicts the enhanced growth of 6-week old LCIA and LCIB transgenic tobacco plants. The larger leave size can easily be spotted in LCIA and LCIB plants compared to wild-type (WT) and non-related transgenic control (T.C.).

DETAILED DESCRIPTION OF THIS INVENTION

The present disclosure pertains to genetically modified higher plants, and subsequent generations thereof, comprising stable or transient expression of at least one gene-product (e.g. mRNA or protein) of the "*Chlamydomonas reinhardtii* $CO_2$ concentrating mechanism", (CCM) wherein the expression takes place in the intermembrane space and/or in one or more subcellular compartments of the chloroplasts of the higher plant, and wherein this expression increases one or more of the characteristics selected from the group of photosynthetic rate, photosynthetic carbon fixation, chlorophyll level and/or biomass of the genetically modified higher plant ($T_0$) and/or of the $T_1$- and/or $T_2$-generation or any further generation of said genetically modified higher plant. In some aspects also faster growth and earlier flowering of said genetically modified higher plant is disclosed.

Wherein the term "higher plants" refers a variety of plants that have the vascular tissues xylem and phloem. The vascular plants include all seed-bearing plants (the gymnosperms and angiosperms) and the pteridophytes (including the ferns, lycophytes, and horsetails). Also called tracheophyte. In one aspect C3-plants are encompassed by this term. In another aspect C4-plants are encompassed.

Wherein the term "stable expression" relates to the sustained expression of a gene (and therefore sustained production of a recombinant protein and/or other gene product) sustained over a period of weeks or months or even years. In one aspect the expression is carried on in subsequent generations, such as $T_1$, $T_2$ and subsequent generations. Thus, the genetic information is carried on in the progenies of the genetically modified higher plant. The integration of the gene may be in the higher plants genome and/or in the genetic information of the chloroplast (Nucleoid) and/or in any other DNA component present in the cell or organelle such like for example a mitochondrion.

The term "transient expression" refers to a temporal expression of a gene (and therefore temporal production of a recombinant protein and/or other gene product) over a shorter time period (hours, days, weeks). Without being exclusively bound to this method, normally transient expression is facilitated by artificial plasmids brought into the cell.

The term "genetically modified higher plant" relates herein to a higher plant, whose genetic material has been altered using genetic engineering techniques. Genetically modified higher plants may be the source of genetically modified foods and are also widely used in scientific research and to produce goods other than food. The term genetically modified higher plant encompasses also the definition "higher plant that possesses a novel combination of genetic material obtained through the use of modern biotechnology".

The term "C3-plants" relates herein to plants that survive solely on C3 fixation. C3 carbon fixation converts carbon dioxide and ribulose bisphosphate (RuBP, a 5-carbon sugar) into 3-phosphoglycerate through the following reaction:

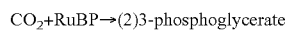

The term "C4-plants" relates herein to plants that use at least one of the potential C4-carbon fixation pathways. In C4-plants the photorespiration pathway, as found in C3-plants, is bypassed. C4 plants have developed a mechanism to more efficiently deliver $CO_2$ to the RuBisCO enzyme. They utilize their specific leaf anatomy where chloroplasts exist not only in the mesophyll cells in the outer part of their leaves but in the bundle sheath cells as well. Instead of direct fixation to RuBisCO in the Calvin cycle, $CO_2$ is incorporated into a 4-carbon organic acid, which has the ability to regenerate $CO_2$ in the chloroplasts of the bundle sheath cells. Bundle sheath cells can then utilize this $CO_2$ to generate carbohydrates by the conventional C3 pathway.

There exist several variants of the C4-pathway:
- The 4-carbon acid transported from mesophyll cells may be malate or aspartate.
- The 3-carbon acid transported back from bundle-sheath cells may be pyruvate or alanine.
- The enzyme that catalyses decarboxylation in bundle-sheath cells differs. In maize and sugarcane, the enzyme is NADP-malic enzyme; in millet, it is NAD-malic enzyme; and, in *Panicum maximum*, it is PEP carboxykinase.

However, the present invention works in any of those variants.

The terms "plant generations", "subsequent generations", "$T_0$ generation", "$T_1$ generation", "$T_2$ generation", relates herein to successive generations of plants following a transformation event. The parent transformed plant is $T_0$, its immediate progeny is $T_1$, and the progeny of the $T_1$ are $T_2$ plants, etc. Subsequent generation may include $T_3$-, $T_4$-, $T_5$- and/or any subsequent generation. However, of particular interest is the stability of transgene expression from $T_0$ to $T_2$, and beyond.

The term "*Chlamydomonas reinhardtii* $CO_2$ concentrating mechanism", (CCM) relates herein to a mechanism for concentrating $CO_2$ as identified in *C. reinhardtii*. CCMs can be based on different biochemical mechanisms such as C4 photosynthesis and crassulaceous acid metabolism (CAM), on active transport of Ci across membranes, or on processes involving localized enhancement of the $CO_2$ concentration by acidification of a particular cellular compartment (Giordano et al., 2005). The role of the CCM is to increase the concentration of $CO_2$ for RuBisCO (ribulose 1,5-bisphosphate carboxylase/oxygenase), the enzyme responsible for the initial fixation of $CO_2$. Thus, CCM may be used in the field for different $CO_2$ concentrating mechanisms. Thus, for clarification it is pointed out that in the present invention use of the term "CCM" always relates only to the CCM of *C. reinhardtii*.

Figure 1:
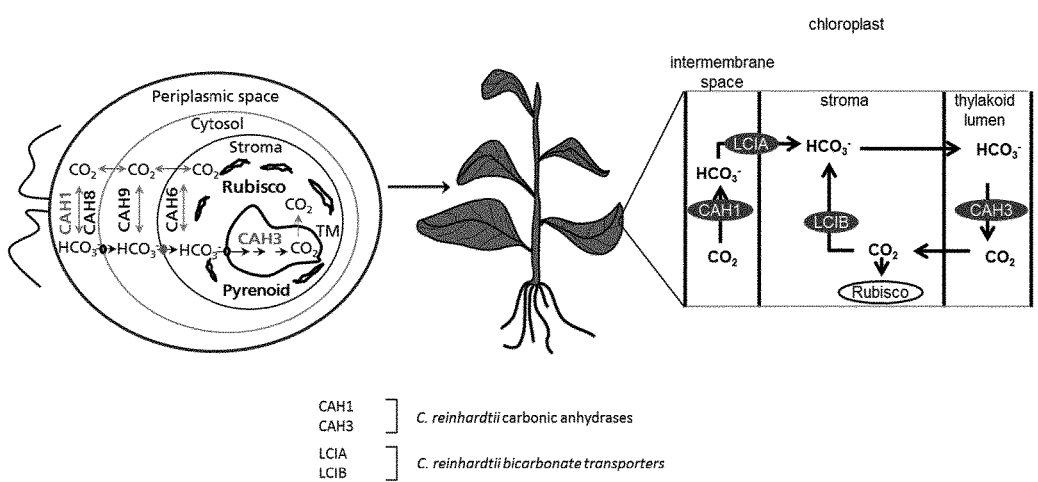
FIG. 1. Integration of *Chlamydomonas reinhardtii* $CO_2$ concentration mechanism (CCM) in higher plants, for example C3-plants FIG. 1 displays the localization of the different CCM-proteines in higher plants, for example a C3-plant. Please note the "atypical" localization of CAH1. CAH1 and CAH3 refer to carbonic anhydrases of *C. reinhardtii*. LCIA and LCIB refer to bicarbonate transporters of *C. reinhardtii*.

A proposed model for concentrating $CO_2$ in *C. reinhardtii* is shown in FIG. 1. The left part of the figure represents the proposed model for the CCM in the *Chlamydomonas*, while the right part of the FIG. 1 represents the inventive strategy in order to integrate enzymes of the $CO_2$ concentration mechanism into the chloroplasts of higher plants. Nuclear encoded carboanhydrases (CAH1 and CAH3) and bicarbonate transporters (CLCIA and LCIB) from *C. reinhardtii* will be expressed at different locations of plant chloroplast to enable an increase of $CO_2$ concentration at the site of RuBisCO. LCIA* indicates the modification of the targeting signal sequence to allow integration of the recombinant protein into the thylakoid membrane.

In this model, the CCM can be divided into two phases. The first phase of the CCM involves acquiring inorganic carbon from the environment and delivering $CO_2$ and HCO$_3$⁻ to the chloroplast. The components of this part of the CCM would include CAs (carbonic anhydrases) in the periplasmic space (CAH1 and possibly CAH8) and a CA in the cytoplasm (CAH9) as well as HCO$_3$⁻ transporters and CO$_2$ channels on both the plasma membrane and the chloroplast envelope. The second part of the proposed model entails the generation of elevated levels of HCO$_3$⁻ in the chloroplast stroma, utilizing the pH gradient across the thylakoid membrane. This part of the CCM includes the CA located in the chloroplast stroma (CAH6) and the CA located within the thylakoid lumen (CAH3) as well as HCO$_3$⁻ transporter(s) on the thylakoid membrane.

It should be emphasized that C. reinhardtii has a strictly C3 biochemistry, since unlike the C4-pathway, wherein transported carbon is stored as organic C4, C. reinhardtii accumulates inorganic carbon, specifically HCO$_3$⁻, in the chloroplast stroma. In addition, while experiments indicate that the marine diatom Thalassiosira weisflogii has a C4-like pathway, the same researchers concluded that a C4-like pathway is unlikely to operate in green algae (Reinfelder et al., 2004).

Besides of a number of CAs which have been shown to be part of the CCM in C. reinhardtii, also some transporters are discussed to play a role in the CCM. Two of those LCIA and LCIB are of particular interest for the present invention.

LCIA is also called NAR1.2. LCIA/NAR1.2 was first annotated as a nitrite transporter and has strong similarity to the bacterial nitrite/formate family of transporters. NAR1.2 belongs to a gene family consisting of six NAR genes in C. reinhardtii, and surprisingly, these genes have no obvious homolog in Arabidopsis or any other higher plants. The expression of NAR1.2 is induced under low-CO$_2$ conditions and is partially under the control of CIA5, a transcription factor that is required for the expression of other CCM genes (Miura et al., 2004). NAR1.2 is predicted to be localized to the chloroplast thylakoid or chloroplast envelope and has six transmembrane domains. The functional expression of NAR1.2 in Xenopus oocytes has shown that the presence of NAR1.2 increases the bicarbonate entry into oocytes two-fold compared to that of the control (Mariscal et al., 2006).

It is part of the present invention that it was found that higher carbonic anhydrase activity could be measured in transgenic lines producing LCIA or LCIB bicarbonate transporters compared to wild type control, indicating that LCIA and LCIB expression affects the activity of endogenous plant carbonic anhydrases.

LCIB does not have any significant homology to proteins from other organisms, but its predicted amino acid sequence has similarity with the predicted amino acid sequence of three genes, LCIC, LCID, and LCIE, in the C. reinhardtii genome. LCIC and LCID are also upregulated under low-CO$_2$ conditions. While these observations pointed to a role for LCIB in the adaptation to low CO$_2$, it was estimated unlikely that LCIB is a transport protein by itself, as it lacks any hydrophobic transmembrane domains. Therefore, LCIB was thought to have a rather regulatory role or might be part of a complex that transports Ci (inorganic carbon (Ci=CO$_2$+ HCO$_3$⁻)) (Van et al. 2001).

The term "intermembrane space" relates to the region between the inner membrane and the outer membrane of a mitochondrion or a chloroplast. The main function of the intermembrane space is oxidative phosphorylation.

This is in contrast to the term "periplasmatic space" which is a space bordered by two selective permeable barriers in Gram-negative bacteria, i.e., biological membranes, which are the inner membrane (i.e. cytoplasmic membrane) and the outer membrane of the Gram-negative bacteria.

The term "subcellular compartments of the chloroplasts" relates herein to the different structural entities of the chloroplast. Whereas in C3-plants, chloroplasts are generally lens-shaped, 5-8 µm in diameter and 1-3 µm thick, greater diversity in chloroplast shapes exists among the algae. The chloroplast in Chlamydomonas for example is rather shaped like a cup.

However, all chloroplasts have at least three membrane systems—the outer chloroplast membrane, the inner chloroplast membrane, and the thylakoid system. Chloroplasts that are the product of secondary endosymbiosis may have additional membranes surrounding these three. Inside the outer and inner chloroplast membranes is the chloroplast stroma, a semi-gel-like fluid that makes up much of a chloroplast's volume, and in which the thylakoid system (thylokoid membrane filled with thylakoid lumen) floats.

Thus, when the terminology "subcellular compartments of the chloroplasts" is used in this invention, this comprises at least the outer chloroplast membrane, the intermembrane space, the inner chloroplast membrane, the chloroplast stroma, the thylakoid membrane and the thylakoid lumen.

The terminology "inner envelope" is used herein sometimes for the inner chloroplast membrane.

The terminology "typical localization" and "atypical localization" refers to the localization of a CCM-related protein, such as for example LCIA, LCIB, CAH1 and CAH3 within source cell or organelle.

With "typical localization" or "native localization" all localizations of the CCM-related protein are encompassed, which resemble the the localization in the compartment of the chloroplast in its natural source, e.g. in C. reinhardtii. This is in contrast to a "atypical" localization, where the CCM-related protein is localized in a compartment of the chloroplast and/or cell, where it cannot be found naturally.

However, the cell compartments in C. reinhardtii and cells of higher plants are sometimes named differently. Thus, the following table should be applied in order to define "resembling compartments" according to the present invention:

TABLE 1

Comparison of compartments

| Compartment in C. reinhardtii | Compartment in Chloroplast of higher Plants |
|---|---|
| Outer (cell–) membrane | Plasma membrane/Plasmalemma |
| Periplasmic space | — |
| Inner (cell–) membrane | Plasma membrane/Plasmalemma |
| Cytoplasm | Cytoplasm |
| Outer chloroplast membrane | Outer chloroplast membrane |
| Intermembrane space | Intermembrane space |
| Inner chloroplast membrane/ Inner envelope | Inner chloroplast membrane/ Inner envelope |
| Stroma | Chloroplast stroma |
| Thylakoid membrane | Thylakoid membrane |
| Pyrenoid | — |

For example: CAH1 is localized in C. reinhardtii in the periplastic space, thus, a localization in the chloroplastic intermembrane space of the gentically modified plant would be considered "atypically". In contrast, the localization of CAH3, LCIA, LCIB is considered "typical" or "native" localization, since they are located in the pyrenoid/thylakoid lumen, chloroplast inner envelope, or chloroplast stroma, respectively.

The terminology "increases one or more of the characteristics selected from the group of photosynthetic rate, photosynthetic carbon fixation, chlorophyll level and/or biomass of the $T_1$ and/or $T_2$ generation of said genetically modified C3-plant and/or C4-plant" relates to increase of any of said characteristics as compared with the non-modified wild-type control plant.

Whereas increase can be between at least 1%, 2%, 3%, 4%, 5%, 6%, 7%, 8%, 9%, 10%, 11%, 12%, 13%, 14%, 15%, 20%, 30%, 40%, 50%, 60%, 70%, 80%, 90%, 100% and up to 5%, up to 10%, up to 15%, up to 20%, up to 25%, up to 30%, up to 40%, up to 50%, up to 60%, up to 70%, up to 80%, up to 90%, up to 95%, up to 99%, up to 100%, up to 110%, up to 120%, up to 130%, up to 140%, up to 150%, up to 160%, up to 170%, up to 180%, up to 190%, up to 200%, up to 250%, up to 260%, up to 270%, up to 280%, up to 290% and/or up to 300%.

However, in some aspects the increase may be at least double (i.e. 100%), triple (i.e. 200%), four times (300%), five times (400%), six times (500%) and up to seven times (600%), eight times (700%), nine times (800%) and ten times (900%) as much as compared to the non-modified wild-type control plant.

If not stated otherwise the measurements herein were done at the end of the vegetative phase of the plant.

In some aspects of the present invention the photosynthetic rates were increased at least by 1%, at least 2%, at least 3%, at least 4%, at least 5%, at least 6%, at least 7%, at least 8%, at least 9%, at least 10%; the levels of chlorophyll were increased by at least 1%, at least 2%, at least 3%, at least 4%, at least 5%, at least 6%, at least 7%, at least 8%, at least 9%, at least 10% and the biomass was increased by at least 10%, at least 20%, at least 30%, at least 40%, at least 50% in the $T_1$- and/or $T_2$-generation and/or subsequent generations as compared to the non-modified wild-type control plant in case of CAH1 expression.

In some aspects of the present invention the photosynthetic rates were increased between 1%-5%, 2%-6%, 3%-7%, 4%-8%, 5%-9%, 6%-10%, 7%-11%, 8%-12%, 9%-13%, 10%-14%; the levels of chlorophyll were increased between 1%-5%, 2%-6%, 3%-7%, 4%-8%, 5%-9%, 6%-10%, 7%-11%, 8%-12%, 9%-13%, 10%-14% and the biomass was increased between 10%-20%, 20%-30%, 30%-40%, 40%-50%, 50%-60%, 60%-70%, 70%-80%, 80%-90%, 90%-100% in the $T_1$- and/or $T_2$-generation and/or subsequent generations as compared to the non-modified wild-type control plant in case of CAH1 expression.

In yet another aspect of the present invention the expression of said carbonic anhydrase CAH1 in the intermembrane space of the chloroplast of the genetically modified higher plant increases the photosynthetic rates by at least 8%, the levels of chlorophyll by at least 7% and/or the biomass by at least 22%, as compared to a wild type control, in the $T_1$ and/or $T_2$ generation or any subsequent generation of said transgenic genetically modified higher plant. Also the leaf number is increased in those plants.

In one aspect of the present invention at the end of vegetative period of the CAH1 $T_2$-plant, three parameters defining biomass are increased as compared to wild-type control:
Leaf area: +22%
Fresh weight: +26%
Dry weight: +29%

In yet another aspect of the present invention the percentage increase at week 3 and at the end of vegetative period of the CAH1 $T_2$-plant is as follows as compared to wild-type control (percentage increase at week 3/percentage increase at end of veg. period; nd: not-determined):

Leaf area: +142%/+22%
Chlorophyll content: +15%/+13%
Leaf number: +21%/+24%
Fresh weight: nd/+26%
Dry weight: nd/+29

In another aspect of the present invention the photosynthetic rates were increased by at least 1%, at least 2%, at least 3%, at least 4%, at least 5%, at least 6%, at least 7%, at least 8%, at least 9%, at least 10% and the levels of chlorophyll by at least 5%, at least 10%, at least 15%, at least 20%, at least 25%, at least 30% and the biomass by at least 10%, at least 20%, at least 30%, at least 40%, at least 50%, at least 60%, at least 70%, at least 80%, at least 90%, at least 100% in the $T_1$ and/or $T_2$ and/or in any subsequent generation as compared to the non-modified wild-type control plant in case of CAH3 expression.

In some aspects of the present invention the photosynthetic rates were increased between 1%-5%, 2%-6%, 3%-7%, 4%-8%, 5%-9%, 6%-10%, 7%-11%, 8%-12%, 9%-13%, 10%-14%; the levels of chlorophyll were increased between 1%-5%, 2%-6%, 3%-7%, 4%-8%, 5%-9%, 6%-10%, 7%-11%, 8%-12%, 9%-13%, 10%-14% and the biomass was increased between 10%-20%, 20%-30%, 30%-40%, 40%-50%, 50%-60%, 60%-70%, 70%-80%, 80%-90%, 90%-100% in the $T_1$- and/or $T_2$-generation and/or subsequent generations as compared to the non-modified wild-type control plant in case of CAH3 expression.

In yet another aspect of the present invention said carbonic anhydrase CAH3 expressed in the thylakoid lumen of the chloroplast of the genetically modified higher plant increases the photosynthetic rates by at least 8%, the levels of chlorophyll by at least 10%, the stomata size is increased by up to 50% and/or the biomass by at least 31% as compared to a wild type control, in the $T_1$ and/or $T_2$ generation or any subsequent generation of said transgenic genetically modified higher plant as compared to wild-type control.

In one aspect of the present invention at the end of vegetative period of the CAH3 $T_2$-plant, three parameters defining biomass are increased as compared to wild-type control:
Leaf area: +24%
Fresh weight: +34%
Dry weight: +31%

In yet another aspect of the present invention the percentage increase at week 3 and at the end of vegetative period of the CAH3 $T_2$-plant is as follows as compared to wild-type control (percentage increase at week 3/percentage increase at end of veg. period; nd: not-determined):
Leaf area: +78%/+24%
Chlorophyll content: +11%/+10%
Leaf number: +26%/+64%
Fresh weight: nd/+34%
Dry weight: nd/+31%

In yet another aspect of the present invention the photosynthetic rates were increased by at least 1%, at least 2%, at least 3%, at least 4%, at least 5%, at least 6%, at least 7%, at least 8%, at least 9%, at least 10%, the levels of chlorophyll by at least 5%, at least 10%, at least 15%, at least 20%, at least 25%, at least 30% and/or biomass by at least 10%, at least 20%, at least 30%, at least 40%, at least 50%, at least 60%, at least 70%, at least 80%, at least 90%, at least 100% in the $T_1$ and/or $T_2$ and/or in any subsequent generation in case of LCIA expression as compared to the non-modified wild-type control plant.

In some aspects of the present invention the photosynthetic rates were increased between 1%-5%, 2%-6%, 3%-7%, 4%-8%, 5%-9%, 6%-10%, 7%-11%, 8%-12%, 9%-13%, 10%-14%; the levels of chlorophyll were increased between 1%-5%, 2%-6%, 3%-7%, 4%-8%, 5%-9%, 6%-10%, 7%-11%, 8%-12%, 9%-13%, 10%-14% and the biomass was increased between 10%-20%, 20%-30%, 30%-40%, 40%-50%, 50%-60%, 60%-70%, 70%-80%, 80%-90%, 90%-100% in the $T_1$- and/or $T_2$-generation and/or subsequent generations as compared to the non-modified wild-type control plant in case of LCIA expression.

In yet another aspect of the present invention the expression of said bicarbonate transporter LCIA in the inner envelope of the chloroplast of the genetically modified higher plant increases the photosynthetic rates by at least 8%, the levels of chlorophyll by at least 15% and/or biomass by at least 33% at the end of the vegetative period, as compared to a wild type control, in the $T_1$ and/or $T_2$ generation or any subsequent generation of said transgenic genetically modified higher plant.

In one aspect of the present invention at the end of vegetative period of the LCIA $T_2$-plant, three parameters defining biomass are increased as compared to wild-type control:
  Leaf area: +33%
  Fresh weight: +54%
  Dry weight: +41%

In yet another aspect of the present invention the percentage increase at week 3 and at the end of vegetative period of the LCIA $T_2$-plant is as follows as compared to wild-type control (percentage increase at week 3/percentage increase at end of veg. period; nd: not-determined):
  Leaf area: +93%/+33%
  Chlorophyll content: +11%/+16%
  Leaf number: +17%/+19%
  Fresh weight: nd/+54%
  Dry weight: nd/+41%

In one aspect of the present invention in case of LCIB expression the biomass was increased at least 10%, at least 20%, at least 30%, at least 40%, at least 50%, at least 60%, at least 70%, at least 80%, at least 90%, at least 100% in the $T_1$ and/or $T_2$ and/or in any subsequent generation as compared to the non-modified wild-type control plant.

In one aspect of the present invention the biomass was increased between 10%-20%, 20%-30%, 30%-40%, 40%-50%, 50%-60%, 60%-70%, 70%-80%, 80%-90%, 90%-100% in the $T_1$- and/or $T_2$-generation and/or subsequent generations as compared to the non-modified wild-type control plant in case of LCIB expression.

In one aspect of the present invention at the end of the vegetative period the leaf area was increased by 23%, the fresh weight was increased by 30%, the dry weight was increased by 28%, the leaf number was increased by 24%, the chlorophyll was increased by 15%.

In yet another aspect of the present invention the expression of said bicarbonate transporter LCIB in the stroma of the chloroplast of the genetically modified higher plant increases the biomass, as compared to a wild type control, in the $T_1$ and/or $T_2$ generation or any subsequent generation of said genetically modified higher plant.

In one aspect of the present invention at the end of vegetative period of the LCIB $T_2$-plant, three parameters defining biomass are increased as compared to wild-type control:
  Leaf area: +23%
  Fresh weight: +30%
  Dry weight: +28%

In yet another aspect of the present invention the percentage increase at week 3 and at the end of vegetative period of the LCIB $T_2$-plant is as follows as compared to wild-type control (percentage increase at week 3/percentage increase at end of veg. period; nd: not-determined):
  Leaf area: +78%/+23%
  Chlorophyll content: +10%/+15%
  Leaf number: +27%/+24%
  Fresh weight: nd/+30%
  Dry weight: nd/+28%

In another aspect at week 6 of the $T_2$ generation of the genetically modified higher plant with LCIB expression the leaf area was increased by 78%, the leaf number was increased by 24% and the chlorophyll was increased by 10%.

In one aspect the leaf area was increased by about 80% in case of CAH3 expression, by about 154% in case of LCIA expression, by about 171% in case of LCIB expression or even by about 260% in case of CAH1 expression.

In another aspect the chlorophyll level was increased by about 6.7% in case of CAH1 expression or about 11.5% in case of LCIA expression.

In yet another aspect leaf area was increased by 22% for CAH1 (P<0.005), 24% for CAH3 (P<0.005), 33% for LCIA (P<0.005) and 23% for LCIB (P<0.005); fresh weight (FW, "fresh weight") was increased by 26% for CAH1 (P<0.005), 34% for CAH3 (P<0.005), 54% for LCIA (P<0.0005) and 30% for LCIB (P<0.005); and dry weight (DW) was increased by 29% for CAH1 (P<0.005), 31% for CAH3 (P<0.005), 41% for LCIA (P<0.005) and 28% for LCIB (P<0.005) as compared to wild-type plants (cf. table 3 in Example section).

For example the following increases could be seen:

For example increase of leaf number (2-6) and surface area (up to 33%); increase of fresh (26-54%) and dry weight (28-54%); in CAH3 and LCIA transgenic lines an increased stomata size (up to 51%), decreased stomata number and density; in CAH3-plants a multiple stem development at early stages; in LCIA lines smoother and larger leaves.

Figure 2:
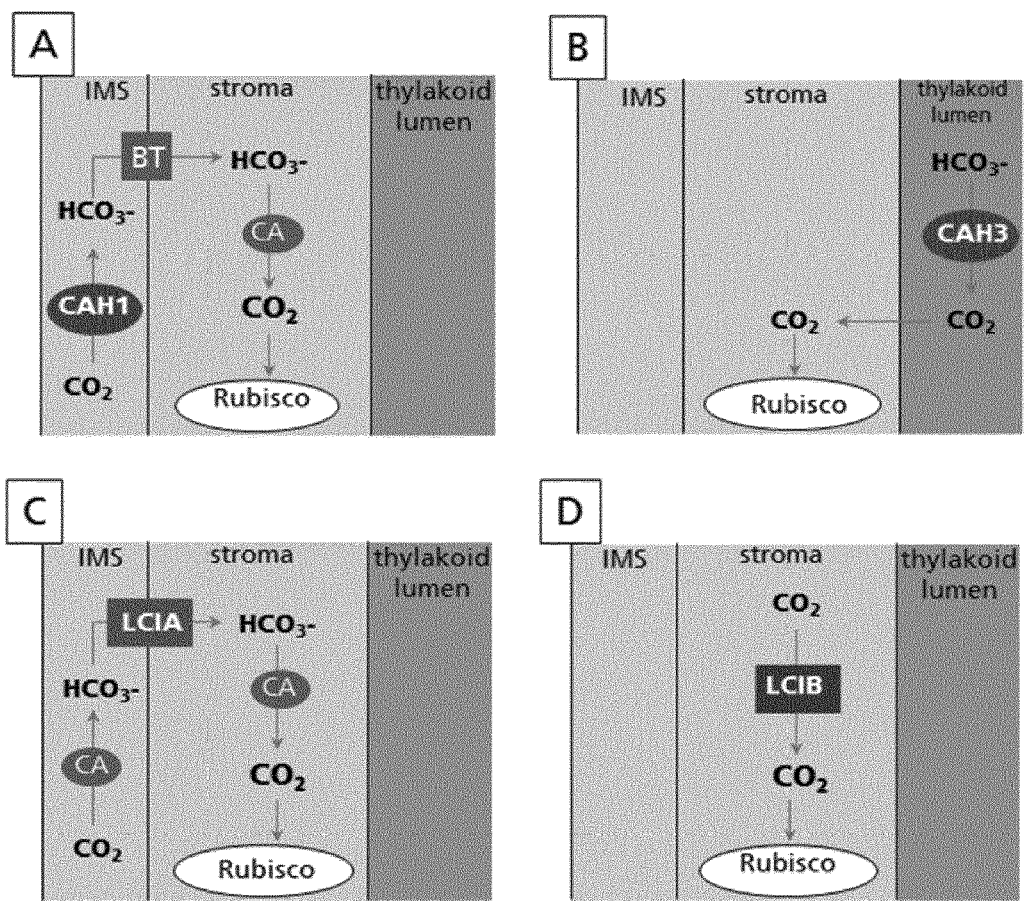
FIG. 2. Expression of *Chlamydomonas* carbonic anhydrases and bicarbonate transporters in tobacco chloroplast ($T_2$ plants)

It becomes clear to the skilled person, that the genetically modified higher plants of the present invention may comprise either single transgenes for CAH1, CAH3, LCIA or LCIB, or any other member of the CCM mechanism (e.g. CAH6), or also several combinations of those transgenes in one plant. E.g. CAH1 and LCIA, CAH3 and LCIB, CAH1 and CAH3, LCIA and LCIB, etc. As the skilled person easily can derive from FIG. 2, the results and the experiments, the genetically modified higher plant can be tailor-made according to the individual needs. Since those combinations have an additional effect, a plant with a single transgene and only slight improved characteristic may be further improved by adding additional transgenes of the CCM mechanism. Thus, this invention also encompasses combinations of two, three or all four of the mentioned CCM species (CAH1, CAH3, LCIA, LCIB) or even the combination with other members of the CCM mechanism (e.g. CAH6).

The calculation of the increases of the plant characteristics mentioned herein may be done by the formula:

$$\text{Increase }[\%] = \frac{(\text{Charact. of gen. mod. plant}) - (\text{Charact. of control plant})}{(\text{Charact. of control plant})} * 100$$

As becomes apparent from above mentioned formula, as long as the same characteristic is tested between the genetically modified plant and the non-modified wild-type control and the same test-systems are used for those tests, the increase in percent is independent of the unit of the characteristic measured.

The specific characteristics which may be increased include photosynthetic rate, photosynthetic carbon fixation, chlorophyll level and/or biomass of the genetically modified higher plant itself ($T_0$) or the $T_1$ and/or $T_2$ generation and/or any further generation of said genetically modified higher plant. As mentioned above, the measurements of characteristics were done herein normally at the end of the vegetative phase of the plant. Wherever it was deviated from this rule, this was explicitly mentioned.

For example the "photosynthetic rate" may be measured by the uptake of $CO_2$, the production of $O_2$, the production of carbohydrates and/or the increase in dry mass (e.g. plant harvested, dried to constant weight and weighed).

For example the "photosynthetic carbon fixation" may be measured by the uptake of trace amounts of $NaH^{14}CO_3$. The incorporation is then determined either by filtration of particulate matter and by measurement of its radioactivity or by the acidification and bubble technique which measures both particulate and dissolved production.

For example the "chlorophyll level" may be measured by spectrophotometry, high performance liquid chromatography (HPLC), and/or fluorometry.

For example the "biomass" may be measured by leaf area, whole plant weight (dry mass, e.g. plant harvested, dried to constant weight and weighed) and/or number of leaves.

The skilled person understands that increase in photosynthetic rates may also result in increased biomass and/or increased carbon fixation and vice versa.

Measurements of the different characteristics may be done (without being bound to those tests) also according to the tests described in the examples section. Suitable tests are for example: Seed weight and number, metabolite analysis, carbon hydrate content such as starch content or sugar content, fresh and dried biomass, etc.

In one aspect any member of the C. reinhardtii CCM may be used to increase the plant characteristics. However, in another aspect the gene-product of the CCM is selected from the group consisting of bicarbonate transporter LCIA, bicarbonate transporter LCIB, carbonic anhydrases CAH1 and/or carbonic anhydrases CAH3 of Chlamydomonas reinhardtii.

In some aspects the gene-product of the CCM is carbonic anhydrase CAH1 of Chlamydomonas reinhardtii stably or transiently expressed in the intermembrane space of the chloroplast of the genetically modified higher plant. In some aspects such an expression in the intermembrane space of the chloroplast increased the levels of chlorophyll by at least 1%, at least 2%, at least 3%, at least 4%, at least 5%, at least 6% at least 7%, at least 8%, at least 9% or at least 10%; and/or the biomass by at least 10%, at least 20%, at least 30%, at least 40%, at least 50%, at least 60%, at least 70%, at least 80%, at least 90%, at least 100% when compared to a non-modified wild-type control plant of same age, same cultivar and raised under same conditions.

In some aspects the gene-product of the CCM is carbonic anhydrase CAH3 of Chlamydomonas reinhardtii stably or transiently expressed in the thylakoid lumen of the chloroplast of the genetically modified higher plant. In some aspects such an expression in the intermembrane space of the chloroplast increased the photosynthetic rates by at least 1%, at least 2%, at least 3%, at least 4%, at least 5%, at least 6% at least 7%, at least 8%, at least 9% or at least 10%; the levels of chlorophyll by at least 10%, at least 11%, at least 12%, at least 13%, at least 14%, at least 15%, at least 16% at least 17%, at least 18%, at least 19%, or at least 20%; and/or the biomass by at least 10%, at least 20%, at least 30%, at least 40%, at least 50%, at least 60%, at least 70%, at least 80%, at least 90%, at least 100% when compared to a non-modified wild-type control plant of same age, same cultivar and raised under same conditions. In some aspects the genetically modified higher plant grows even faster and/or has a shorter vegetative phase as compared to a wild-type control.

In some aspects the gene-product of the CCM is bicarbonate transporter LCIA of Chlamydomonas reinhardtii stably or transiently expressed in the intermembrane space of the chloroplast of the genetically modified higher plant. In some aspects such an expression in the inner envelope of the chloroplast of the chloroplast increased the photosynthetic rates by at least 1%, at least 2%, at least 3%, at least 4%, at least 5%, at least 6% at least 7%, at least 8%, at least 7%, at least 9% or at least 10%; the levels of chlorophyll by at least 10%, at least 11%, at least 12%, at least 13%, at least 14%, at least 15%, at least 16% at least 17%, at least 18%, at least 19%, or at least 20%; and/or the biomass by at least 10%, at least 20%, at least 30%, at least 40%, at least 50%, at least 60%, at least 70%, at least 80%, at least 90%, at least 100% when compared to a non-modified wild-type control plant of same age, same cultivar and raised under same conditions.

In some aspects the gene-product of the CCM is bicarbonate transporter LCIB of Chlamydomonas reinhardtii stably or transiently expressed in the intermembrane space of the chloroplast of the genetically modified higher plant. In some aspects such an expression in the stroma of the chloroplast increased the biomass by at least 10%, at least 20%, at least 30%, at least 40%, at least 50%, at least 60%, at least 70%, at least 80%, at least 90%, at least 100% when compared to a non-modified wild-type control plant of same age, same cultivar and raised under same conditions.

The present invention also pertains to methods for producing a genetically modified higher plant as described herein.

Furthermore, the present invention also pertains to the use of the genetically modified higher plant in order to increase the production rate of a natural and/or transgenic product produced by said modified genetically modified higher plant as compared to the wild-type control.

Such a "natural product" may be a flower, a seed, a fruit, a vegetable, a nut, an oil, a protein, a peptide, a nucleic acid, a metabolite such as an alcohol, an antioxidant, organic acid, polyol, an amino acid, a vitamin and/or a nucleotide; wood, fibers, leaves, or any other thing which is produced in increased amounts by said modified organic plant and can be harvested from this plant. Normally such a natural product is a commercially useful part of the plant.

The skilled person understands that the present invention can be applied both to a C3- as well as a C4-plant.

Examples for C3-plants include rice, wheat, orange tree, wine plant, coffee plant, tobacco plant, tea plant, peanut plant, lemon tree, potato, carrot, tomato plant, peach tree, apple tree, pear tree, mango tree and barley; the natural product harvested from such plant could be for example rice grains, wheat grains, orange fruits, grapes, coffee-beans, tobacco leaves, tea leaves and buds, peanuts, lemons, potatoes, carrots, tomatoes, peaches, apples, pears, mango or barley grains, etc.

Further examples include oats, rye, triticale, dry bean, soybean, mung bean, faba bean, cowpea, common pea, chickpea, pigeon pea, lentil, banana, coconut, taro, yams, sweet potato, cassava, sugar beet, cotton, jute, sisal, sesame, sunflower, rapeseed and safflower.

Further examples include cereals, legumes, fruits, roots and tubers, oil crops, fibre crops and trees.

With respect to C4-plants the examples include any product derived from crab grass, corn (maize), amaranth, sorghum, millet, sugarcane, nut grass, crab grass, barnyard grass, fourwinged salt bush and chenopods.

However, such natural products also include for example amylopectin derived from rice, starch derived from potatoes, nicotine derived from tobacco, caffeine derived from coffee or tea plants, etc.

In some aspects biodiesel and/or bioethanol may be produced from the genetically modified higher plants according to the present invention.

A "transgenic product" includes any product which is not naturally produced in wild-type plants, but produced because a nucleic acid comprising one or more genes encoding for a gene product have been introduced into the plant by transgenic and/or biotechnological means additional to the genetic modification which resulted in the increase of the plants characteristic.

Such a transgenic product includes a nucleic acid, a protein, a peptide and/or any other metabolite normally not produced by this plant such as an alcohol, an antioxidant, organic acid, polyol, an amino acid, a vitamine and/or a nucleotide. In some aspects the transgenic product may include a pharmaceutical active substance, also called active ingredient (AI), active pharmaceutical ingredient (API) or sometimes also phytopharmaceutical.

As active ingredient (AI) any substance is comprised that is biologically active. Such an ingredient may be used in animal or human medicine, or may for example be a pesticide, fungicide, antibiotics or the like.

For example in one aspect a vaccine, an enzyme, an antibody and/or a hormone is produced by the modified plant.

This invention pertains also to uses of the method to the increase of one or more of the characteristics selected from the group of photosynthetic rate, photosynthetic carbon fixation, chlorophyll level and/or biomass in the $T_1$ and/or $T_2$ and/or in any subsequent generation of a genetically modified higher plant.

Such uses may include the increase the capability of resistance or durability of a genetically modified higher plant in order to increase the sustainability in their natural environment. In other aspects the method is used to increase the capability of resistance or durability of a genetically modified higher plant in order to allow the growth of that plant under conditions too harsh for the wild-type control plant.

In some aspects the use of the method is encompassed in order to create a genetically modified genetically modified higher plant which is able to grow under climate and/or nutritional conditions which do not allow the growth of a wild-type control.

In other aspects the genetically modified higher plant belongs to the class of Dicotyledons, to the order of Solanales, to the family of Solanaceae and/or to the genus *Nicotiana*. In one aspect the genetically modified higher plant is a tobacco plant (*Nicotiana tabacum*).

The term "nucleic acid molecule" or "nucleic acid" is intended to indicate any single- or double stranded nucleic acid molecule of cDNA, genomic DNA, synthetic DNA or RNA, peptide nucleic acid (PNA) or LNA origin.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein.

Thus, the term "mutations" also refers to all of the changes in the polypeptide sequence encoded by the polynucleic acid sequence modified by one or more of the above described changes.

The present disclosure is also directed to vectors comprising a nucleotide molecule of the present disclosure. The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

In general, those skilled in the art are well able to construct vectors and design protocols for recombinant gene expression.

Vector constructs and expression systems are well known in the art and may be adapted to incorporate use of recombinant fusion polypeptides provided herein. For example, transgenic plant production is known and generation of constructs and plant production maybe adapted according to known techniques in the art. In some aspects, transient expression systems in plants are desirable.

In general, standard methods known in the art may be used for culturing or growing plants, plant cells, and/or plant tissues in accordance with the invention (e.g. clonal plants, clonal plant cells, clonal roots, clonal root lines, sprouts, sprouted seedlings, plants, etc.) for biomass production or production of recombinant polypeptides and metabolites, respectively.

In some aspects of the present disclosure, it will be desirable to isolate recombinant polypeptide(s), for example for vaccine products, enzymes, antibodies, hormones, or the like.

Where a protein in accordance with the disclosure is produced from plant tissue(s) or a portion thereof, e.g., roots, root cells, plants, plant cells, that express them, methods known in the art may be used for any of partial or complete isolation from plant material. Where it is desirable to isolate the expression product from some or all of plant cells or tissues that express it, any available purification techniques maybe employed. Those of ordinary skill in the art are familiar with a wide range of fractionation and separation procedures (see, for example, Scopes et al., Protein Purification Principles and Practice, 3rd Ed, Janson et al, 1993, Protein Purification Principles High Resolution Methods, and Inventions, Wiley-VCH, 1998, Springer-Verlag, NY, 1993, and Roe, Protein Purification Techniques, Oxford University Press, 2001, each of which is incorporated herein by reference). Those skilled in the art will appreciate that a method of obtaining desired recombinant fusion polypeptide(s) product(s) is by extraction. Plant material (e.g., roots, leaves, etc.) may be extracted to remove desired products from residual biomass, thereby increasing the concentrating and purity of product. Plants may be extracted in a buffered solution. For example, plant material may be transferred into an amount of ice-cold water at a ratio of one to one by weight that has been buffered with, e.g., phosphate buffer. Protease inhibitors can be added as required. The plant material can be disrupted by vigorous blending or grinding while suspended in buffer solution and extracted biomass removed by filtration or centrifugation. The product earned in solution can be further purified by additional steps or converted to a dry powder by freeze-drying or precipitation. Extraction can be earned out by pressing plants or roots in a press or by being crushed as they are passed through closely spaced rollers. Fluids derived from crushed plants or roots are collected and processed according to methods well known in the art. Extraction by pressing allows release of products in a more concentrated form. In some aspects, polypeptides can be further purified by chromatographic methods including, but not limited to anion exchange chromatography (Q-Column) or ultrafiltration. Polypeptides that contain His-tags can be purified using nickel-exchange chromatography according to standard methods. In some aspects, produced proteins or polypeptides are not isolated from plant tissue but rather are provided in the context of live plants (e.g., sprouted seedlings). In some aspects, where the plant is edible, plant tissue containing expressed protein or polypeptide is provided directly for consumption. Thus, the present disclosure provides edible young plant biomass (e.g. edible sprouted seedlings) containing expressed protein or polypeptide.

Further processing steps such as purification steps may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

Furthermore, the isolated and purified polypeptide of interest may be further processed, such as e.g. formulated into a composition, e.g. a pharmaceutical composition.

In the present context, the term "process" may be used interchangeably with the terms "method" or "procedure" and refers in particular to any assembly and/or order of procedural steps for purifying a recombinant produced fusion protein according to the present disclosure.

The term "multi-step" process is in the present context employed to describe a process for purifying a protein and/or a peptide, which comprises a series of costly and/or laborious and/or time-consuming and/or technically complicated purification steps. As a general rule, a multi-step process, in contrast to the process described in the methods of the present disclosure with one or only a few number of steps, comprises at least two distinctly separated procedural steps for the initial disruption of the host cell and for the first crude separation of the heterologous protein from host cell proteins and contaminants. Typically, these steps are again followed by at least one purification step. Although both the multi-step process and the process related to in the present disclosure may further comprise several additional purification steps, if need for even higher purity of the protein of interest arises, this is not essential for the process described in the present disclosure. The process of the present disclosure, generating substantially pure recombinant fusion proteins that are practically free from contaminating host cell proteins, can preferably be performed in essentially a single procedural step.

EXAMPLES

In the following examples, materials and methods of the present disclosure are provided. It should be understood that these examples are for illustrative purpose only and are not to be construed as limiting this disclosure in any manner. All publications, patents, and patent inventions cited herein are hereby incorporated by reference in their entirety for all purposes.

Example 1: Synthesis of *Chlamydomonas reinhardtii* CAH1, CAH3, LCIA and LCIB cDNAs The coding sequences for CAH1 (GenBank: D90206.1), CAH3 (GenBank: U73856), LCIA (GenBank: AY612639.1) and LCIB (GenBank: AB168093.1) from *Chlamydomonas reinhardtii* were obtained by chemical DNA synthesis (Genscript, Piscataway, USA). Prior to synthesis, each of the cDNAs was codon optimized for maximum expression yields according to *Nicotiana tabacum* codon usage. In addition a generic algorithm was used to optimize the synthetic cDNAs simultaneously for a large set of competing parameters, such as mRNA secondary structure, cryptic splice sites, codon and motif repeats, and homogenous GC content. The synthesized CAH3, LCIA and LCIB cDNAs contained their native transit peptide sequence from *C. reinhardtii*, enabling targeting of the recombinant CAH3, LCIA and LCIB proteins into the thylakoid lumen, the chloroplast inner membrane and the stroma, respectively. The synthesized CAH1 cDNA contained the transit peptide sequence of Tic22 from *Arabidopsis thaliana*, enabling the targeting of the recombinant CAH1 protein into the inner membrane space, an atypical localization for *C. reinhardtii* CAH1. Each of the synthesized constructs contained the 5'-untranslated region of the *Petrosilium chalcone* synthase gene, upstream of the CAH1, CAH3, LCIA or LCIB cDNA and the tag54 encoding sequence downstream. The synthesized four cDNAs were transferred separately to the vector pUC18 via the restriction enzyme sites EcoRI and XbaI.

Example 2: Subcloning of CAH1, CAH3, LCIA and LCIB, Respectively, into the Plant Expression Vector To evaluate the in vivo effect of the *C. reinhardtii* CAH1, CAH3, LCIA or LCIB, respectively, on carbonic anhydrase activity and biomass production in *N. tabacum* cv. *Petit Havana* SR1 plants, each of the cDNAs encoding CAH1, CAH3, LCIA or LCIB were inserted separately into a plant expression vector pTRA alone or fused to the EmGFP cDNA. Transgene expression was driven by the Cauliflower mosaic virus 35S promoter with dublicated enhancer region. The pTRA plasmid contained the scaffold attachment region of the tobacco RB7 gene (gi3522871) and the nptII cassette of pPCV002 (Konz et Shell, 1986) for selection of transgenic plants on kanamycin-containing agar plates. The final constructs were designated:

pTRA-35S-AtTic22-TP:CAH1, pTRA-35S-AtTic22-TP:CAH1-GFP,
pTRA-35S-CrTL-TP:CAH3, pTRA-35S-CrTL-TP:CAH3-GFP
pTRA-35S-CrIM-TP:LCIA, pTRA-35S-CrIM-TP:LCIA-GFP
pTRA-35S-CrS-TP:LCIB, pTRA-35S-CrS-TP:LCIB-GFP

In the following as an example for a plant expression vector the sequence of pTRA-35S-AtTic22-TP:CAH1 (SEQ ID NO. 5 (8882 bps)) is disclosed:

```
aattccgccc ctagaaatat ttgcgactct tctggcatgt aatatttcgt taaatatgaa     60
gtgctccatt tttattaact ttaaataatt ggttgtacga tcactttctt atcaagcgtt    120
actaaaatgc gtcaatctct ttgttcttcc atattcatat gtcaaaatct atcaaaattc    180
ttatatatct ttttcgaatt tgaagtgaaa tttcgataat ttaaaattaa atagaacata    240
tcattattta ggtgtcatat tgatttttat acttaattac taaatttggt taactttgaa    300
agtgtacatc aacgaaaaat tagtcaaacg actaaaataa ataaatatca tgtgttatta    360
agaaaattct cctataagaa tattttaata gatcatatgt ttgtaaaaaa aattaatttt    420
tactaacaca tatatttact tatcaaaaat ttgacaaagt aagattaaaa taatattcat    480
ctaacaaaaa aaaaccagaa aatgctgaaa acccggcaaa accgaaccaa tccaaaccga    540
tatagttggt ttggtttgat tttgatataa accgaaccaa ctcggtccat ttgcacccct    600
aatcataata gctttaatat ttcaagatat tattaagtta acgttgtcaa tatcctggaa    660
attttgcaaa atgaatcaag cctatatggc tgtaatatga atttaaaagc agctcgatgt    720
ggtggtaata tgtaatttac ttgattctaa aaaaatatcc caagtattaa taatttctgc    780
taggaagaag gttagctacg atttacagca aagccagaat acaaagaacc ataaagtgat    840
tgaagctcga aatatacgaa ggaacaaata ttttttaaaaa aatacgcaat gacttggaac    900
aaaagaaagt gatatatttt ttgttcttaa acaagcatcc cctctaaaga atggcagttt    960
tcctttgcat gtaactatta tgctcccttc gttacaaaaa ttttggacta ctattgggcg   1020
cggggcgcgc ccggtccaaa gaccagaggg ctattgagac ttttcaacaa agggtaatat   1080
cgggaaacct cctcggattc cattgcccag ctatctgtca cttcatcgaa aggacagtag   1140
aaaaggaaga tggcttctac aaatgccatc attgcgataa aggaaaggct atcgttcaag   1200
atgcctctac cgacagtggt cccaaagatg gacccccacc cacgaggaac atcgtggaaa   1260
aagaagacgt tccaaccacg tcttcaaagc aagtggattg atgtgataca tggtggagca   1320
cgacactctc gtctactcca agaatatcaa agatacagtc tcagaagacc agagggctat   1380
tgagactttt caacaaaggg taatatcggg aaacctcctc ggattccatt gcccagctat   1440
ctgtcacttc atcgaaagga cagtagaaaa ggaagatggc ttctacaaat gccatcattg   1500
cgataaagga aaggctatcg ttcaagatgc ctctaccgac agtggtccca aagatggacc   1560
cccacccacg aggaacatcg tggaaaaaga gacgttcca accacgtctt caaagcaagt   1620
ggattgatgt gatatctcca ctgacgtaag ggatgacgca caatcccact atccttcgca   1680
agacccttcc tctatataag gaagttcatt tcatttggag aggacacgct gaattcacta   1740
cacagattag attcatcgaa agattcatca agaagaagaa aactatggag tcaagcgtta   1800
agccaaaccc attcctctca ttttcttctt ttattcatca ccaatgtact agattcagta   1860
gcgatttgag tgctagaatc gaagatacaa agaggtttgc tgagactctt gcaacaagaa   1920
ggttttcttt gcctactcca cctccattcg cttccgtttc catggggtgt atctataagt   1980
tcggtactag cccagattcc aaagcaacag tgtctggaga tcattgggat cacggactta   2040
atggtgaaaa ctgggaggga aaagatggag ctggtaatgc atgggtgtgc aagacaggta   2100
gaaagcaatc accaattaat gttccacaat atcaggtgtt ggatggaaag ggttcaaaaa   2160
ttgctaatgg tcttcaaact cagtggagtt accctgattt gatgtctaac ggaacatcag   2220
```

-continued

```
ttcaagttat taataacgga catactatac aagttcagtg gacatacaac tacgctggtc    2280
atgcaactat tgctatccca gcaatgcaca atcaaacaaa caggattgtt gatgtgcttg    2340
aaatgagacc taatgatgct gcagataggg ttactgctgt gccaacacag tttcacttcc    2400
attcaactag tgaacatctt ttggcaggaa agatctatcc tttagagctc catatagttc    2460
accaagtgac tgaaaagctt gaggcttgta aaggaggttg ctttagtgtt acaggaatcc    2520
ttttccagtt ggataatggt ccagataacg aactccttga acctatattc gctaatatgc    2580
caagtagaga aggtactttc agcaacttac ctgcaggaac tacaattaag ctcggagagc    2640
ttttgccatc tgatagggat tatgttactt acgaaggatc tcttactaca cctccatgtt    2700
ctgagggttt actctggcat gtgatgacac aacctcagag aatttctttt ggacagtgga    2760
atagatacag attagctgtt ggtctcaaag aatgcaactc aactgagaca gctgcagatg    2820
ctggacatca ccatcaccat agaaggcttt tgcacaatca tgcacactta gaagaggttc    2880
ctgctgcaac tagcgaacca aagcattatt ttagaagagt tatgcttgct gagtctgcaa    2940
atccagatgc atacacatgc aaagctgttg cattcggtca aaactttagg aaccctcagt    3000
atgctaacgg aagaactatc aagctcgcta ggtatcataa acatctgaaa gattgggaac    3060
atctggaaga atttgcggcc gctcatcacc atcaccatca ctagctcgag ctcggatcct    3120
ctagagtccg caaaaatcac cagtctctct ctacaaatct atctctctct attttctcc    3180 agaataatgt gtgagtagtt cccagataag ggaattaggg ttcttatagg gtttcgctca    3240
tgtgttgagc atataagaaa cccttagtat gtatttgtat ttgtaaaata cttctatcaa    3300
taaaatttct aattcctaaa accaaaatcc agtgaccggg cggccggccg ccctagaaa    3360 tatttgcgac tcttctggca tgtaatattt cgttaaatat gaagtgctcc atttttatta    3420
actttaaata attggttgta cgatcacttt cttatcaagc gttactaaaa tgcgtcaatc    3480
tctttgttct tccatattca tatgtcaaaa tctatcaaaa ttcttatata tcttttttcga    3540 atttgaagtg aaatttcgat aatttaaaat taaatagaac atatcattat ttaggtgtca    3600
tattgatttt tatacttaat tactaaattt ggttaacttt gaaagtgtac atcaacgaaa    3660
aattagtcaa acgactaaaa taaataaata tcatgtgtta ttaagaaaat tctcctataa    3720
gaatatttta atagatcata tgtttgtaaa aaaattaat ttttactaac acatatattt    3780
acttatcaaa aatttgacaa agtaagatta aaataatatt catctaacaa aaaaaaacca    3840
gaaaatgctg aaaacccggc aaaaccgaac caatccaaac cgatatagtt ggtttggttt    3900
gattttgata taaaccgaac caactcggtc catttgcacc cctaatcata atagctttaa    3960
tatttcaaga tattattaag ttaacgttgt caatatcctg gaaattttgc aaaatgaatc    4020
aagcctatat ggctgtaata tgaatttaaa agcagctcga tgtggtggta atatgtaatt    4080
tacttgattc taaaaaaata tcccaagtat taataatttc tgctaggaag aaggttagct    4140
acgatttaca gcaaagccag aatacaaaga accataaagt gattgaagct cgaaatatac    4200
gaaggaacaa atatttttaa aaaaatacgc aatgacttgg aacaaaagaa agtgatatat    4260
tttttgttct taaacaagca tcccctctaa agaatggcag ttttcctttg catgtaacta    4320
ttatgctccc ttcgttacaa aaattttgga ctactattgg gcgggtggag ggggatcaga    4380
ttgtcgtttc ccgccttcag tttaaactat cagtgtttga caggatatat tggcgggtaa    4440
acctaagaga aaagagcgtt tattagaata atcggatatt taaaagggcg tgaaaaggtt    4500
tatccgttcg tccatttgta tgtgtacatc accgacgagc aaggcaagac cgagcgcctt    4560
tccgacgctc accgggctgg ttgccctcgc cgctgggctg gcggccgtct atggccctgc    4620
```

-continued

```
aaacgcgcca gaaacgccgt cgaagccgtg tgcgagacac cggccgccgg cgttgtggat    4680
acctcgcgga aaacttggcc ctcactgaca gatgaggggc ggacgttgac acttgagggg    4740
ccgactcacc cggcgcggcg ttgacagatg aggggcaggc tcgatttcgg ccggcgacgt    4800
ggagctggcc agcctcgcaa atcggcgaaa acgcctgatt ttacgcgagt ttcccacaga    4860
tgatgtggac aagcctgggg ataagtgccc tgcggtattg acacttgagg ggcgcgacta    4920
ctgacagatg aggggcgcga tccttgacac ttgaggggca gagtgctgac agatgagggg    4980
cgcacctatt gacatttgag gggctgtcca caggcagaaa atccagcatt tgcaagggtt    5040
tccgcccgtt tttcggccac cgctaacctg tcttttaacc tgcttttaaa ccaatattta    5100
taaaccttgt ttttaaccag ggctgcgccc tgtgcgcgtg accgcgcacg ccgaaggggg    5160 gtgcccccc ttctcgaacc ctcccggccc gctaacgcgg gcctccatc cccccagggg    5220 ctgcgcccct cggccgcgaa cggcctcacc ccaaaaatgg cagcgctggc agtccttgcc    5280
attgccggga tcggggcagt aacgggatgg gcgatcagcc cgacaagcta cccctatttg    5340 tttattttc taaatacatt caaatatgta tccgctcatg agacaataac cctgataaat    5400
gcttcaataa tattgaaaaa ggaagagtat gagtattcaa catttccgtg tcgcccttat    5460 tcccttttt gcggcatttt gccttcctgt ttttgctcac ccagaaacgc tggtgaaagt    5520
aaaagatgct gaagatcagt tgggtgcacg agtgggttac atcgaactgg atctcaacag    5580
cggtaagatc cttgagagtt ttcgccccga agaacgtttt ccaatgatga gcacttttaa    5640
agttctgcta tgtggcgcgg tattatcccg tattgacgcc gggcaagagc aactcggtcg    5700
ccgcatacac tattctcaga atgacttggt tgagtactca ccagtcacag aaaagcatct    5760
tacggatggc atgacagtaa gagaattatg cagtgctgcc ataaccatga gtgataacac    5820
tgcggccaac ttacttctga caacgatcgg aggaccgaag gagctaaccg cttttttgca    5880
caacatgggg gatcatgtaa ctcgccttga tcgttgggaa ccggagctga atgaagccat    5940
accaaacgac gagcgtgaca ccacgatgcc tgtagcaatg gcaacaacgt tgcgcaaact    6000
attaactggc gaactactta ctctagcttc ccggcaacaa ttaatagact ggatggaggc    6060
ggataaagtt gcaggaccac ttctgcgctc ggcccttccg gctggctggt ttattgctga    6120
taaatctgga gccggtgagc gtgggtctcg cggtatcatt gcagcactgg ggccagatgg    6180
taagccctcc cgtatcgtag ttatctacac gacggggagt caggcaacta tggatgaacg    6240
aaatagacag atcgctgaga taggtgcctc actgattaag cattggtaac tgtcagacca    6300
agtttactca tatatacttt agattgattt aaaacttcat ttttaattta aaaggatcta    6360
ggtgaagatc ctttttgata atctcatgac caaaatccct aacgtgagt tttcgttcca    6420 ctgagcgtca gaccccgtag aaaagatcaa aggatcttct tgagatcctt ttttttctgcg    6480 cgtaatctgc tgcttgcaaa caaaaaaacc accgctacca gcggtggttt gtttgccgga    6540
tcaagagcta ccaactcttt ttccgaaggt aactggcttc agcagagcgc agataccaaa    6600
tactgtcctt ctagtgtagc cgtagttagg ccaccacttc aagaactctg tagcaccgcc    6660
tacatacctc gctctgctaa tcctgttacc agtggctgct gccagtggcg ataagtcgtg    6720
tcttaccggg ttggactcaa gacgatagtt accggataag gcgcagcggt cgggctgaac    6780
ggggggttcg tgcacacagc ccagcttgga gcgaacgacc tacaccgaac tgagatacct    6840
acagcgtgag ctatgagaaa gcgccacgct tcccgaaggg agaaaggcgg acaggtatcc    6900
ggtaagcggc agggtcggaa caggagagcg cacgagggag cttccagggg gaaacgcctg    6960
gtatctttat agtcctgtcg ggtttcgcca cctctgactt gagcgtcgat ttttgtgatg    7020
ctcgtcaggg gggcggagcc tatggaaaaa cgccagcaac gcggcctttt tacggttcct    7080
```

-continued

```
ggccttttgc tggccttttg ctcacatgga ctctagctag aggatcacag gcagcaacgc  7140
tctgtcatcg ttacaatcaa catgctaccc tccgcgagat catccgtgtt tcaaacccgg  7200
cagcttagtt gccgttcttc cgaatagcat cggtaacatg agcaaagtct gccgccttac  7260
aacggctctc ccgctgacgc cgtcccggac tgatgggctg cctgtatcga gtggtgattt  7320
tgtgccgagc tgccggtcgg ggagctgttg gctggctggt ggcaggatat attgtggtgt  7380
aaacaaattg acgcttagac aacttaataa cacattgcgg acgtttttaa tgatcgaata  7440
ctaacgtctc taccagatat cagcttgcat gccggtcgat ctagtaacat agatgacacc  7500
gcgcgcgata atttatccta gtttgcgcgc tatattttgt tttctatcgc gtattaaatg  7560
tataattgcg ggactctaat cataaaaacc catctcataa ataacgtcat gcattacatg  7620
ttaattatta catgcttaac gtaattcaac agaaattata tgataatcat cgcaagaccg  7680
gcaacaggat tcaatcttaa gaaactttat tgccaaatgt ttgaacgatc tgcttgactc  7740
tagctagagt ccgaaccccca gagtcccgct cagaagaact cgtcaagaag gcgatagaag  7800
gcgatgcgct gcgaatcggg agcggcgata ccgtaaagca cgaggaagcg gtcagcccat  7860
tcgccgccaa gctcttcagc aatatcacgg gtagccaacg ctatgtcctg atagcggtcc  7920
gccacaccca gccggccaca gtcgatgaat ccagaaaagc ggccatttc caccatgata  7980 ttcggcaagc aggcatcgcc ctgggtcacg acgagatcct cgccgtcggg catccgcgcc  8040
ttgagcctgg cgaacagttc ggctggcgcg agccctgat gctcttcgtc cagatcatcc  8100
tgatcgacaa gaccggcttc catccgagta cgtcctcgct cgatgcgatg tttcgcttgg  8160
tggtcgaatg ggcaggtagc cggatcaagc gtatgcagcc gccgcattgc atcagccatg  8220
atggatactt tctcggcagg agcaaggtga gatgacagga gatcctgccc cggcacttcg  8280
cccaatagca gccagtccct tcccgcttca gtgacaacgt cgagcacagc tgcgcaagga  8340
acgcccgtcg tggccagcca cgatagccgc gctgcctcgt cttggagttc attcagggca  8400
ccggacaggt cggtcttgac aaaaagaacc gggcgcccct gcgctgacag ccggaacacg  8460
gcggcatcag agcagccgat tgtctgttgt gcccagtcat agccgaatag cctctccacc  8520
caagcggccg gagaacctgc gtgcaatcca tcttgttcaa tcatgcctcg atcgagttga  8580
gagtgaatat gagactctaa ttggataccg aggggaattt atggaacgtc agtggagcat  8640
ttttgacaag aaatatttgc tagctgatag tgaccttagg cgactttga acgcgcaata  8700 atggtttctg acgtatgtgc ttagctcatt aaactccaga aacccgcggc tgagtggctc  8760
cttcaacgtt gcggttctgt cagttccaaa cgtaaaacgg cttgtcccgc gtcatcggcg  8820
ggggtcataa cgtgactccc ttaattctcc gctcatgatc gatatccatt gaagagcaag  8880 ct
```

Example 3: Tobacco Plant Transformation and Regeneration

The plant expression vectors were introduced into *Agrobacterium tumefaciens* GV3101 (pMP90RK, GmR, KmR, RifR) cells using a Gene Pulser II electroporation system (BioRad, Hercules, Calif., USA) according to the manifacturer's instructions. Leaf discs from 4-5-week-old wild-type tobacco (*N. tabacum* cv. *Petit Havana* SR1) plants were transformed by infection with recombinant *A. tumefaciens* carrying binary vectors indicated above (Dietze et al., 1995). Calli were grown on Murashige-Skoog medium containing 50 mg/L kanamycin and plants were regenerated from resistant calli. Potential transgenic plants were transferred to soil in the glasshouse, and then selfed to produce $T_1$ generation. Transgenic tobacco plants were cultivated in the greenhouse in DE73 standard soil in 13-L pots with a 16-h natural daylight photoperiod and 22° C. day-time/20° C. day/night-time temperature.

Up to 25 transgenic $T_0$ lines (named CAH1-1 to CAH1-25; CAH1-GFP-1 to CAH1-GFP25; CAH3-1 to CAH3-25; CAH3-GFP-1 to CAH3-GFP25; LCIA-1 to LCIA-25; LCIA-GFP-1 to LCIA-GFP-25; LCIB-1 to LCIB-25 and LCIB-GFP-1 to LCIB-GFP-25) were screened for the presence of the transgenes integrated into genome using PCR. PCR analysis confirmed the presence of the transgenes in all analyzed transgenic lines. Accumulation of the transcript and recombinant proteins, respectively, was demonstrated by using RT-PCR and immunoblot analysis. For immunoblot analysis, the upper fully-expanded leaves from 5-week-old tobacco plants were ground to a fine powder under liquid nitrogen, and total soluble protein (TSP) was extracted with two volumes of extraction buffer (50 mM Tris-HCl, pH 8, 100 mM NaCl, 10 mM dithiothreitol (DTT), 5 mM ethylenediaminetetraacetic acid (EDTA) and 0.1% (v/v) Tween-20). The extracts were centrifuged at 8500×g for 20 min at 4° C. and used for immunoblot analysis. Recombinant CAH1, CAH3, LCIA and LCIB proteins were detected with a rabbit anti-Tag54 monoclonal antibody (RAb-Tag54; 200 ng/ml). In addition, CAH3 protein was also detected with the rabbit anti-CAH3 polyclonal antibody (1:2000 dilution in 1×PBS) (Antibody-online, Aachen, Germany). The band intensities of the recombinant proteins were quantified using Aida software (Raytest, Straubenhardt, Germany) against known concentrations of a bacterial affinity-purified scFv as a standard.

While the LCIB recombinant protein was produced in all transgenic $T_0$ lines, only 25% and 75% of the regenerated lines showed detectable levels of the CAH1 or LCIA protein at the expected molecular size of 51.6 kDa and 36.5 kDa, respectively. The recombinant CAH3 protein production was not detectable in the analysed $T_0$ plants, obviously due to the low accumulation levels and/or the low sensitivity of the detection antibody. The recombinant CAH1-GFP, CAH3-GFP, LCIA-GFP and LCIB-GFP proteins were produced in all analyzed transgenic $T_0$ lines.

Transgenic CAH1, LCIA and LCIB lines with the highest levels of the recombinant protein accumulation following the Mendelian segregation were selected for establishment of the $T_1$ generation. Since CAH3 accumulation was under immunoblot detection levels, we selected three PCR positive $T_0$ lines following the Mendelian segregation for establishment of CAH3 $T_1$ generation. The presence of the CAH1, CAH3, LCIA and LCIB insert was confirmed in all twenty-five analyzed $T_1$ plants per construct by PCR. Furthermore the CAH3 transcript presence was also confirmed by RT-PCR analysis in 75% of CAH3 transgenic $T_1$ lines. The accumulation of the recombinant CAH1, CAH3, LCIA and LCIB was similar to the parental $T_0$ lines. The insert presence and the recombinant protein accumulation were also confirmed in the $T_2$ generation by RT-PCR (FIG. 3) and immunoblot (FIG. 4). While CAH3 accumulation was increased to 1 µg/g fresh weight in $T_2$ generation, the accumulation of the recombinant CAH1, LCIA and LCIB was similar to the parental lines (CAH1: 5 µg/g fresh weight; LCIA: 100 µg/g fresh weight; LCIB 40 µg/g fresh weight).

Example 4: Analysis of Carbonic Anhydrase Activity

To investigate whether the CAH1 and CAH3 carbonic anhydrases are active in plants, total carbonic anhydrase activity was measured in 6-week-old transgenic $T_2$ plants accumulating the highest levels of the recombinant proteins according to the potentiometric method described by Wilbur and Anderson (1948). Twenty µL of serial dilution (50-375 Units) of carbonic anhydrase enzyme solution from bovine erythrocytes (Sigma Aldrich, Germany) or plant extract from transgenic and wild type control was added to 1.48 ml of 20 nM Veronal buffer (727 mM NaCl, 9.12 mM Na-diethyl-barbiturate 15.63 mM 5,5'-diethyl barbiture acid) (pH 8.3) in a chamber maintained at 4° C. The reaction was initiated by addition of 0.5 ml of ice-cold $CO_2$-saturated water and the time required for the pH to drop from 8.3 to 8.0 was determined. The WA unit of activity was defined as follows: WA unit=Tc/T–1 were Tc and T are the time required for the pH to drop in the absence and presence of enzyme solution, respectively.

Wild-type tobacco plants and non-related transgenic control (transgenic $T_2$ tobacco plants producing the human antibody M12) assayed under the same conditions showed significant background activity due to the activity of endogenous carbonic anhydrases (FIG. 6). Extract preparations from the CAH1 and CAH3 plants produced significantly more carbonic anhydrase activity (208% and 188%, respectively) than the wild-type plants (FIG. 6), indicating that the engineered CAH1 and CAH3 possessed carbonic anhydrase activity. Furthermore, a significant increase (183% and 179%) in the carbonic anhydrase activity was also observed in the leaf extract of transgenic plants producing recombinant LCIA or LCIB, respectively, indicating that constitutive expression of the C. reinhardtii bicarbonate transporters lead to enhanced activity of endogenous tobacco carbonic anhydrases. Therefore, we conclude that the engineered recombinant CAH1, CAH3, LCIA and LCIB were functional in transgenic $T_1$ and $T_2$ plants.

Example 5: Photosynthetic Activity of Transgenic Tobacco Plants

The impact of recombinant CAH1, CAH3, LCIA and LCIB on the photosynthetic performance of the transgenic tobacco plants was determined by monitoring gas-exchange parameters. Fully-expanded upper leaves from 7-8 weeks-old $T_1$ and $T_2$ tobacco plants were used for gas exchange measurements using the LI-6400 system (Li-Cor, Bad Homburg, Germany). The following parameters were used: photon flux density 1,000 mmol m$^{-2}$ s$^{-1}$, chamber temperature 26° C., flow rate 150 mmol s$^{-1}$, relative humidity 60-70%.

The $CO_2$ compensation point (F) was determined by measuring the photosynthesis rates at 400, 300, 200, 100, 80, 60 and 40 ppm $CO_2$. The apparent $CO_2$ compensation point (F) was deduced from A/Ci curves by regression analysis in the linear range of the curve. Measurements were taken from the same plants after 4 h light on two different following days. As indicated in FIG. 13, the apparent photosynthetic rate (A) in selected CAH1-, CAH3-, LCIA- and LCIB-producing lines increased by 12.4, 14, 9 and 10%, respectively, under ambient conditions (400 ppm $CO_2$, 21% 02, 24° C.), suggesting that the increased photosynthetic rate in the transgenic lines reflects the greater availability of $CO_2$ in the vicinity of RiBisCO. Transgenic CAH3- and LCIA-producing plants were also characterized by a significant ($p<0.01$) reduction in the apparent $CO_2$ compensation point (3% and 2%, respectively), indicating a higher rate of photosynthesis. The CAH1- and LCIB-producing $T_1$ and $T_2$ lines also showed a tendency to reduce the $CO_2$ compensation points. Furthermore, the stomata conduction was significantly increased by 27% and 33% in CAH3- and LCIA-producing lines, respectively, indicating higher levels of $CO_2$ entering into the plant cell.

In FIG. 13, the enhanced photosynthesis in transgenic plants is shown. Analyses were performed when plants were 7-8-weeks old. N WT=7; n CAH1=8; n CAH3=10; n LCIA=11; n LCIB=3.

Example 6: Leaf Starch Analysis in Transgenic Plants

To determine the impact of C. reinhardtii carbonic anhydrases and bicarbonate transporters on primary carbon metabolism, we evaluated the ability of transgenic $T_2$ lines and wild-type plants to accumulate photosynthesic end products. To determine starch levels, 50 mg leaf material was collected at two different time points, at the beginning and at the end of the illumination period. The frozen leaf material was ground in liquid nitrogen and resuspended in 80% (v/v) ethanol. The extract was mixed for 10 min at 80° C. and centrifuged for 20 min at 4000 g. The pellet was resuspended in 80% (v/v) and 50% (v/v) ethanol, respectively, followed by mixing at 80° C. and centrifugation as above. The resulting pellet was washed with 90% (v/v) ethanol, resuspended in 400 μL 0.2 KOH and incubated at 95° C. for 1 h. Finally, samples were mixed with 70 μL 1 M acetic acid and the starch content was measured enzymatically. The leaves of all lines contained low levels of starch early in the morning but significant increases (up to 2.67 fold increase, $p<0.005$ in LCIA-producing $T_2$ lines) were observed by the end of the day in transgenic lines compared to wild-type control. The higher increase in the starch measured in all transgenic lines reflected the improved $CO_2$ assimilation which was sufficient to support not only the growth but also the accumulation of storage compounds in the leaves, which are then mobilized to provide carbon for growth during the night.

Example 7: Assessment of Phenotype of Plants Accumulating *C. reinhardtii* CAH1, CAH3, LCIA or LCIB Growth of the transgenic plants accumulating CAH1, CAH3, LCIA or LCIB in the chloroplast, was monitored weekly in the $T_1$ and $T_2$ generations by measurements of the leaf number, plant height and leaf area according to the formula:

$$\text{Leaf area}(cm^2) = 3.73 \times (\text{length} \times \text{width}/100) + 0.011 \times (\text{length} \times \text{width}/100)^2.$$

Transgenic tobacco $T_2$ lines producing one of the recombinant proteins showed a significant increase of the leaf area during the complete growth period (Table 2) when compared to non-transgenic control plants and non-related transgenic control. In addition, transgenic plants had more leaves (2-6 leaves more), grew much faster in the early stages of development (Leaf area: CAH1: 260% increase, CAH3: 69% increase, LCIA: 154% increase and LCIB: 171% increase at the age of 5 weeks old). The faster growth led to earlier (1.5-2 weeks compared to wild-type and non-related transgenic control) seed production.

TABLE 2

| | | % increase comparing with the wild-type | | | |
|---|---|---|---|---|---|
| | | CAH1 | LCIA | CAH3 | LCIB |
| Week 5 | Leaf area | 260** | 154** | 69** | 171** |
| | Chlorophyll content | 7* | n.s. | 12** | n.s. |
| | Leaf number | 33** | 27** | 13** | 27** |
| | Height | 400** | 360** | 100** | 350** |
| Week 6 | Leaf area | 142** | 93** | 78** | 78** |
| | Chlorophyll content | 15** | 11** | 11** | 10** |
| | Leaf number | 21* | 17* | 8 | 25* |
| | Height | 235** | 207** | 107** | 148** |
| Week 7 | Leaf area | 53** | 56** | 41** | 33** |
| | Chlorophyll content | 13** | 8** | 12** | 10** |
| | Leaf number | 36** | 29** | 19* | 29** |
| | Height | 102** | 92** | 49** | 45** |

TABLE 2-continued

| | | % increase comparing with the wild-type | | | |
|---|---|---|---|---|---|
| | | CAH1 | LCIA | CAH3 | LCIB |
| Week 8 | Leaf area | 22* | 33* | 24** | 23 n.s. |
| | Chlorophyll content | 13*** | 16*** | 10*** | 15*** |
| | Leaf number | 24** | 19* | 11 | 24* |
| | Height | 3 | 68** | 60** | 46* |
| | Fresh weight | 26* | 54** | 34* | 30* |
| | Dry weight | 29 | 41* | 31* | 28* |

*$P < 0.005$;
**$P < 0.0005$;
***$P < 0.00005$;
n.s. non significant

The dry and fresh weight was monitored in the $T_2$ generation when plants were 8 week-old. As indicated in Table 3, all transgenic lines showed a significant increase of the fresh and dry weight ranging from 26% to 54% at the end of the vegetative period.

TABLE 3

| | % increase[1] | | |
|---|---|---|---|
| | Leaf area | FW | DW |
| CAH1 | 22* | 26* | 29* |
| CAH3 | 24* | 34* | 31* |
| LCIA | 33* | 54** | 41* |
| LCIB | 23* | 30 | 28* |

Notes:
[1]at the end of vegetative period
*$P < 0.005$;
**$P < 0.0005$

Example 8: Nitrogen Starvation Study

The wild-type, homozygous LCIA and LCIB transgenic $T_4$ line were grown hydroponically for 4 weeks on MS medium containing 100% nitrogen and for 2 additional weeks in low-nitrogen (75% less nitrogen than normal MS medium). The 6-week-old LCIA and LCIB transgenic plants (2 weeks after nitrogen starvation) showed a significant increase in the fresh and dry shoot weights (FIG. 18; Table 4) compared to wild-type plants. Interestingly, we observed a significant increase in the fresh and dry root weight as well (LCIA: 32%, 17%; LCIB: 56% and 45%, respectively; Table 4)). At this time point, nitrate reductase activity was assayed, which is the most important enzyme in the assimilation of nitrate (the predominant form of nitrogen available to green plants growing in soil). Transgenic LCIA and LCIB transgenic plants showed significant increase in the nitrate reductase activity (LCIA: 48% and LCIB: 45%) compared to the wild-type plants (FIG. 19).

There was no significant difference in the shoot or root fresh and dry weights, or nitrate reductase activity between the wild-type and the non-related transgenic controls, suggesting that the significant changes observed are due solely to LCIA and LCIB expression. These data indicate that the constitutive expression of LCIA or LCIB in the tobacco chloroplast potentially increases the efficiency of the nitrogen assimilation in LCIA and LCIB transgenic plants.

TABLE 4

| | % increase[1] | | | | |
|---|---|---|---|---|---|
| | Shoot | | Root | | |
| | FW | DW | FW | DW | Roots |
| LCIA | 93* | 68* | 32* | 17* | 44* |
| LCIB | 118* | 81* | 56* | 45* | 67* |

*P < 0.05

FIG. 18. Enhanced growth of $T_4$ transgenic lines grown in hydroponic cultures under nitrogen depletion (75% less nitrogen). FIG. 18, depicts the enhanced growth of 6-week old LCIA and LCIB transgenic tobacco plants. The larger leave size can easily be spotted in LCIA and LCIB plants compared to wild-type (WT) and non-related transgenic control (T.C.).

FIG. 19. Nitrate reductase activity of hydroponically grown plants under nitrogen starvation conditions expressed as micromoles of $NO_2^-$ per gram fresh weight (FW) per minute. Data are means±SD (n=5). * p<0.05

REFERENCES

The contents of all cited references, including literature references, issued patents, and published patent inventions, as cited throughout this invention are hereby expressly incorporated by reference.

Dietze et al., 1995, *Agrobacterium*-mediated transformation of potato (*Solanum tuberosum*). In I Potrykus, G Spangenberg, eds, Gene Transfer to Plants, Springer Laboratory Manual. Springer, Berlin, pp 24-29

Giordano, M., J. Beardall, and J. A. Raven. 2005. $CO_2$ concentrating mechanisms in algae: mechanisms, environmental modulation, and evolution. Annu. Rev. Plant Biol. 56:99-131.

Reinfelder, J. R., A. M. L. Kraiepiel, and F. M. M. Morel. 2004. The role of the C4 pathway in carbon accumulation and fixation in a marine diatom. Plant Physiol. 135:2106-2111

Janson et al, 1993, Protein Purification Principles High Resolution Methods, and Inventions, Wiley-VCH, 1998, Springer-Verlag, NY, 1993

Konz et Shell, 1986 The promoter of TL-DNA gene 5 controls the tissue-specific expression of chimaeric genes carried by a novel type of *Agrobacterium* binary vector. Mol Gen Genet 204:383-396

Mariscal, V., P. Moulin, M. Orsel, A. J. Miller, E. Fernández, and A. Galván. 2006. Differential regulation of the *Chlamydomonas* Nar1 gene family by carbon and nitrogen. Protist 157:421-433

Miura, K., T. Yamano, S. Yoshioka, T. Kohinata, Y. Inoue, F. Taniguchi, E. Asamizu, Y. Nakamura, S. Tabata, K. T. Yamato, K. Ohyama, and H. Fukuzawa. 2004. Expression profiling-based identification of CO2-responsive genes regulated by CCM1 controlling a carbon-concentrating mechanism in *Chlamydomonas reinhardtii*. Plant Physiol. 135:1595-1607

Roe, Protein Purification Techniques, Oxford University Press, 2nd Ed., 2001

Scopes et al, Protein Purification Principles and Practice, Springer, 3rd Ed.

Van, K., Y. Wang, Y. Nakamura, and M. H. Spalding. 2001. Insertional mutants of *Chlamydomonas reinhardtii* that require elevated $CO_2$ for survival. Plant Physiol. 127:607-614

Wilbur and Anderson (1948) Electrometric and colorimetric determination of carbonic anhydrase. J Biol Chem 176 147-154

What is claimed is:

1. A genetically modified higher plant, and/or a subsequent generation thereof, comprising stable and/or transient expression of at least one gene-product of the "Chlamydomonas reinhardtii $CO_2$ concentration mechanism" (CCM), wherein said at least one gene-product of the "Chlamydomonas reinhardtii $CO_2$ concentration mechanism" (CCM) is selected from the group consisting of bicarbonate transporter LCIB, carbonic anhydrase CAH1, and carbonic anhydrase CAH3 of Chlamydomonas reinhardtii and wherein the expression takes place in the intermembrane space and/or one or more subcellular compartments of the chloroplasts of the higher plant.

2. The genetically modified higher plant according to claim 1, wherein a $T_1$ and/or $T_2$ generation or a subsequent generation of the genetically modified higher plant grows faster, produces more biomass and/or has a shorter vegetative phase as compared to a wild-type control.

3. The genetically modified higher plant according to claim 1, wherein said gene-product of the "*Chlamydomonas reinhardtii* $CO_2$ concentration mechanism" (CCM) is said carbonic anhydrase CAH1 of *Chlamydomonas reinhardtii*, in particular wherein said carbonic anhydrase CAH1 is expressed in the intermembrane space of the chloroplast of the higher plant, in particular wherein the expression of said carbonic anhydrase CAH1 in the intermembrane space of the chloroplast of the higher plant increases photosynthetic rate, level of chlorophyll, and/or dry weight biomass measured at an end of a vegetative period, as compared to a wild-type control, in a $T_1$ and/or $T_2$ generation or any subsequent generation of said transgenic higher plant.

4. The genetically modified higher plant according to claim 1, wherein said gene-product of the "*Chlamydomonas reinhardtii* $CO_2$ concentration mechanism" (CCM) is said carbonic anhydrase CAH3 of *Chlamydomonas reinhardtii*, in particular wherein said carbonic anhydrase CAH3 is expressed in a thylakoid lumen of the chloroplast of the higher plant, in particular wherein the expression of said carbonic anhydrase CAH3 in the thylakoid lumen of the chloroplast of the genetically modified higher plant increases photosynthetic rate, level of chlorophyll, and/or biomass, as compared to a wild-type control, in a $T_1$ and/or $T_2$ generation or a subsequent generation of said genetically modified higher plant.

5. The genetically modified higher plant according to claim 1, wherein said gene-product of the "*Chlamydomonas reinhardtii* $CO_2$ concentration mechanism" (CCM) is said bicarbonate transporter LCIB of *Chlamydomonas reinhardtii*, in particular wherein said bicarbonate transporter LCIB is expressed in a stroma of the chloroplast of the genetically modified higher plant, in particular wherein the expression of said bicarbonate transporter LCIB in the stroma of the chloroplast of the higher plant increases biomass, as compared to a wild-type control, in a $T_1$ and/or $T_2$ generation or a subsequent generation of said genetically modified higher plant.

6. A method for producing a genetically modified higher plant according to claim 1, the method comprising generating a plant expression vector comprising a nucleic acid sequence encoding said gene-product and transforming the higher plant with the plant expression vector.

7. A method of using the genetically modified higher plant according to claim 1 in order to increase production rate of a natural and/or transgenic product produced by said genetically modified higher plant as compared to the wild-type control, the method comprising providing the genetically modified higher plant and cultivating the plant under conditions permitting increased production rate of a natural and/or transgenic product.

8. The method according to claim 7, wherein the natural product produced by the genetically modified higher plant is selected from the group consisting of a flower, a fruit, a seed, and a nut.

9. The method according to claim 7, wherein the transgenic product produced by the genetically modified higher plant is selected from the group consisting of a nucleic acid, a protein, a peptide, and a metabolic product produced with transgenic means.

10. The method according to claim 6, wherein the genetically modified higher plant has an increase of one or more characteristic selected from the group consisting of photosynthetic rate, photosynthetic carbon fixation, chlorophyll level and/or biomass in a $T_1$ and/or $T_2$ and/or in any subsequent generation of the genetically modified higher plant.

11. The method according to claim 6, wherein the genetically modified higher plant is able to grow under climate and/or nutritional conditions which do not allow growth of a wild-type control or growth with lower efficiency.

12. The genetically modified higher plant according to claim 1, wherein said genetically modified higher plant is a C3- or C4-plant.

13. The genetically modified higher plant according to claim 1, wherein the genetically modified higher plant is selected from the group consisting of rice, wheat, orange tree, wine plant, coffee plant, tobacco plant, tea plant, peanut plant, lemon tree, potato, carrot, tomato, peach tree, apple tree, pear tree, mango tree, barley, oats, rye, triticale, dry bean, soybean, mung bean, faba bean, cowpea, common pea, chickpea, pigeon pea, lentil, banana, coconut, taro, yams, sweet potato, cassava, sugar beet, cotton, jute, sisal, sesame, sunflower, rapeseed, safflower, crab grass, corn (maize), amaranth, sorghum, millet, sugarcane, nut grass, crab grass, barnyard grass, fourwinged salt bush, and a chenopod.

14. The genetically modified higher plant according to claim 13, wherein the genetically modified higher plant is the tobacco plant (*Nicotiana tabacum*).

15. A genetically modified higher plant, and/or a subsequent generation thereof, comprising stable and/or transient expression of a gene-product of the "*Chlamydomonas reinhardtii* $CO_2$ concentration mechanism" (CCM), wherein the gene-product comprises:
 a. carbonic anhydrase CAH1 expressed in an intermembrane space of a chloroplast of the genetically modified higher plant,
 b. carbonic anhydrase CAH3 expressed in a thylakoid lumen of the chloroplast of the higher plant,
 c. bicarbonate transporter LOB expressed in a stroma of the chloroplast of the genetically modified higher plant, and
 d. bicarbonate transporter LCIA expressed in an inner envelope of the chloroplast of the genetically modified higher plant.

16. A method for producing a genetically modified higher plant according to claim 15, the method comprising generating a plant expression vector comprising a nucleic acid sequence encoding said gene-product and transforming the higher plant with the plant expression vector.

17. The method according to claim 15, wherein the genetically modified higher plant has an increase of one or more characteristic selected from the group consisting of photosynthetic rate, photosynthetic carbon fixation, chlorophyll level and/or biomass in a $T_1$ and/or $T_2$ and/or in any subsequent generation of the genetically modified higher plant.

18. The method according to claim 15, wherein the genetically modified higher plant is able to grow under climate and/or nutritional conditions which do not allow growth of a wild-type control or growth with lower efficiency.

* * * * *